United States Patent
Dombrowski et al.

(10) Patent No.: US 7,671,053 B2
(45) Date of Patent: Mar. 2, 2010

(54) BENZAMIDE INHIBITORS OF THE P2X$_7$ RECEPTOR

(75) Inventors: Mark A. Dombrowski, Waterford, CT (US); Allen J. Duplantier, Ledyard, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 12/147,212

(22) Filed: Jun. 26, 2008

(65) Prior Publication Data

US 2009/0042886 A1 Feb. 12, 2009

Related U.S. Application Data

(63) Continuation of application No. 11/620,969, filed on Jan. 8, 2007, now Pat. No. 7,407,956, which is a continuation of application No. 11/260,075, filed on Oct. 27, 2005, now Pat. No. 7,176,202, which is a continuation of application No. 10/748,340, filed on Dec. 30, 2003, now Pat. No. 6,974,812.

(60) Provisional application No. 60/437,505, filed on Dec. 31, 2002.

(51) Int. Cl.
*C07D 253/075* (2006.01)
*A61K 31/53* (2006.01)
*A61P 11/06* (2006.01)

(52) U.S. Cl. ..................... 514/242; 544/182
(58) Field of Classification Search ................ 544/182; 514/242

See application file for complete search history.

(56) References Cited

U.S. PATENT DOCUMENTS

| | | | |
|---|---|---|---|
| 5,948,803 A | 9/1999 | Maeda et al. | |
| 5,961,376 A | 10/1999 | Gottschald | |
| 7,176,202 B2 * | 2/2007 | Dombroski et al. | 514/242 |
| 7,407,956 B2 * | 8/2008 | Dombroski et al. | 514/242 |

OTHER PUBLICATIONS

Dowd et al., British Journal of Pharmacology 125(2): 341-346, 1998.( PubMed Abstract).*
Goldbalt et al., Clin. Exp. Immunol. 140(2): 195-204, 2005. (PubMed Abstract).*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Dowd et al., "P2X Receptor-Mediated Excitation of Nociceptive Afferents in the Normal and Arthritic Rat Knee Joint", British Journal of Pharmacology, 1998, pp. 341-346, vol. 125 No. 2.
Goldbalt, et al., "New Therapies for Rheumatoid Arthritis", Clin Exp Immunol, 2005, vol. 140 No. 2, pp. 195-204.
West, Anthony R, et al., "Solid State Chemistry and its Applications", Wiley, New York, 1988, pp. 358 & 365.
Vippagunta, et al., "Crystalline Solids", Advanced Drug Delivery Reviews, 2001, vol. 48, pp. 3-26.

* cited by examiner

*Primary Examiner*—Venkataraman Balasubramanian
(74) *Attorney, Agent, or Firm*—Pfizer, Inc.; Julie M. Lappin

(57) ABSTRACT

The present invention provides benzamide inhibitors of the P2X$_7$ receptor of the formula:

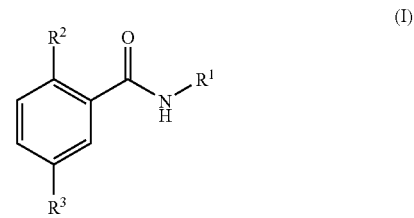

(I)

wherein $R^1$-$R^3$ are as defined herein. The compounds of the invention are useful in the treatment of IL-1 mediated disorders, including, without limitation, inflammatory diseases such as osteoarthritis and rheumatoid arthritis; allergies, asthma, COPD, cancer, reperfusion or ischemia in stroke or heart attack, autoimmune diseases and other disorders.

3 Claims, No Drawings

BENZAMIDE INHIBITORS OF THE P2X$_7$ RECEPTOR

CROSS-REFERENCE TO RELATED APPLICATIONS

This application is a Continuation application, which claims priority to U.S. application Ser. No. 11/620,969, filed Jan. 8, 2007, now U.S. Pat. No 7,407,956, issued Aug. 5, 2008, which claims priority to U.S. application Ser. No. 11/260,075, filed Oct. 27, 2005, now U.S. Pat. No. 7,176,202, issued Feb. 13, 2007, which claims priority to U.S. application Ser. No. 10/748,340, filed Dec. 30, 2003, now U.S. Pat. No. 6,974,812, issued Dec. 13, 2005, which claims priority to U.S. Provisional Application No. 60/437,505, filed Dec. 31, 2002.

BACKGROUND OF THE INVENTION

The present invention relates to novel benzamide inhibitors of the P2X$_7$ receptor, processes for their preparation, intermediates useful in their preparation, pharmaceutical compositions containing them, and their use in therapy. The active compounds of the present invention are useful in the treatment of inflammatory diseases such as osteoarthritis and rheumatoid arthritis; allergies, asthma, COPD, cancer, reperfusion or ischemia in stroke or heart attack, autoimmune diseases and other disorders. The active compounds are also antagonists of the P2X$_7$ receptor.

The P2X$_7$ receptor (previously known as P2Z receptor), which is a ligand-gated ion channel, is present on a variety of cell types, largely those known to be involved in inflammatory/immune process, specifically, macrophages, mast cells and lymphocytes (T and B). Activation of the P2X$_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis, and L-selectin shedding (lymphocytes). P2X$_7$ receptors are also located on antigen-presenting cells (APC), keratinocytes, salivary acinar cells (parotid cells), hepatocytes and mesangial cells.

P2X$_7$ antagonists are known in the art, such as those described in International Patent Publications WO 01/46200, WO 01/42194, WO 01/44213, WO99/29660, WO 00/61569, WO 99/29661, WO 99/29686, WO 00/71529, and WO 01/44170, as well as in U.S. Ser. No. 60/336,781, filed Nov. 12, 2002).

Benzamides, heteroarylamides and reverse amides for uses other than inhibition of the P2X$_7$ receptor are described in various publications, such as International Patent Publications WO 97/22600, EP 138,527, WO 00/71509, WO 98/28269, WO 99/17777 and WO 01/58883.

SUMMARY OF THE INVENTION

The present invention relates to a compound of the formula

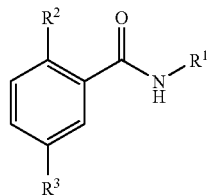

(I)

wherein R$^1$ is (C$_1$-C$_6$)alkyl, optionally substituted by (C$_3$-C$_{10}$)cycloalkyl, (C$_6$-C$_{10}$)aryl, (C$_1$-C$_{10}$)heterocyclyl, or (C$_1$-C$_{10}$)heteroaryl, wherein each of said (C$_1$-C$_6$)alkyl, (C$_3$-C$_{10}$)cycloalkyl, (C$_6$-C$_{10}$)aryl, (C$_1$-C$_{10}$)heterocyclyl, or (C$_1$-C$_{10}$)heteroaryl are optionally substituted by one to three suitable moieties independently selected from the group consisting of hydroxy, halogen, CN—, (C$_1$-C$_6$)alkyl, HO(C$_1$-C$_6$)alkyl, (C$_1$-C$_6$)alkyl-NH(C=O)—, NH$_2$(C=O)—, (C$_1$-C$_6$)alkoxy, or (C$_3$-C$_{10}$)cycloalkyl, wherein said (C$_3$-C$_{10}$C)cycloalkyl is optionally substituted by one or more moieties selected from halogen, or (C$_1$-C$_6$)alkyl-;

R$^2$ is hydrogen, halogen, —CN, and (C$_1$-C$_6$)alkyl, wherein said (C$_1$-C$_6$)alkyl is optionally substituted by one to three suitable moieties, independently selected from the group consisting of halo, hydroxy, amino, —CN, (C$_1$-C$_6$)alkyl, (C$_1$-C$_6$)alkoxy, —CF$_3$, CF$_3$O—, (C$_1$-C$_6$)alkyl-NH—, [(C$_1$-C$_6$)alkyl]$_2$-N—, (C$_1$-C$_6$)alkyl-S—, (C$_1$-C$_6$)alkyl-(S=O)—, (C$_1$-C$_6$)alkyl-(SO$_2$)—, (C$_1$-C$_6$)alkyl-O—(C=O)—, formyl, (C$_1$-C$_6$)alkyl-(C=O)—, and (C$_3$-C$_6$)cycloalkyl; and R$^3$ is a suitably substituted nitrogen linked (C$_1$-C$_{10}$)heterocyclyl of the formula:

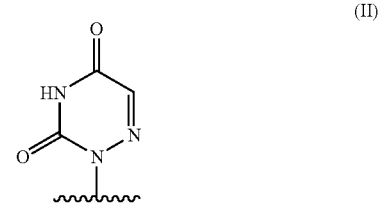

(II)

or the pharmaceutically acceptable salts or solvates or prodrugs thereof.

The present invention also relates to a compound of the formula

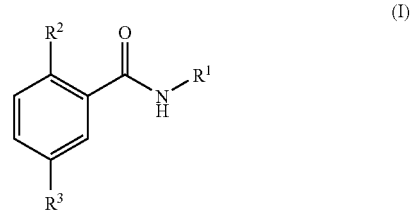

(I)

wherein R$^1$ is (C$_1$-C$_6$)alkyl, optionally substituted by (C$_3$-C$_{10}$)cycloalkyl, (C$_6$-C$_{10}$)aryl, (C$_1$-C$_{10}$)heterocyclyl, or (C$_1$-C$_{10}$)heteroaryl, wherein each of said (C$_1$-C$_6$)alkyl, (C$_3$-C$_{10}$)cycloalkyl, (C$_6$-C$_{10}$C)aryl, (C$_1$-C$_{10}$)heterocyclyl, or (C$_1$-C$_{10}$)heteroaryl are optionally substituted by one to three suitable moieties independently selected from the group consisting of hydroxy, halogen, CN—, (C$_1$-C$_6$)alkyl, HO(C$_1$-C$_6$)alkyl, (C$_1$-C$_6$)alkyl-NH(C=O)—, NH$_2$(C=O)—, (C$_1$-C$_6$)alkoxy, or (C$_3$-C$_{10}$)cycloalkyl, wherein said (C$_3$-C$_{10}$)cycloalkyl is optionally substituted by one or more moieties selected from halogen, or (C$_1$-C$_6$)alkyl-;

R$^2$ is hydrogen, halogen, —CN, and (C$_1$-C$_6$)alkyl, wherein said (C$_1$-C$_6$)alkyl is optionally substituted by one to three suitable moieties, independently selected from the group consisting of halo, hydroxy, amino, —CN, (C$_1$-C$_6$)alkyl, (C$_1$-C$_6$)alkoxy, —CF$_3$, CF$_3$O—, (C$_1$-C$_6$)alkyl-NH—, [(C$_1$-C$_6$)alkyl]$_2$-N—, (C$_1$-C$_6$)alkyl-S—, (C$_1$-C$_6$)alkyl-(S=O)—, (C$_1$-C$_6$)alkyl-(SO$_2$)—, (C$_1$-C$_6$)alkyl-O—(C=O)—, formyl, (C$_1$-C$_6$)alkyl-(C=O)—, and (C$_3$-C$_6$)cycloalkyl;

R³ is a nitrogen linked (C₁-C₁₀)heterocyclyl of the formula:

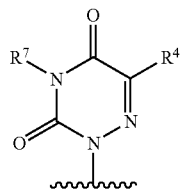

(III)

wherein R⁴ is selected from the group of suitable substituents, such as hydrogen, halo, hydroxy, —CN, HO—(C₁-C₆)alkyl, (C₁-C₆)alkyl optionally substituted with one to three fluoro, (C₁-C₆)alkoxy optionally substituted with one to three fluoro, HO₂C—, (C₁-C₆)alkyl-O—(C═O)—, R⁵R⁶N(O₂S)—, (C₁-C₆)alkyl-(O₂S)—NH—, (C₁-C₆)alkyl-O₂S—[(C₁-C₆)alkyl-N]—, R⁵R⁶N(C═O)—, R⁵R⁶N(CH₂)ₘ—, (C₆-C₁₀)aryl, (C₃-C₈)cycloalkyl, (C₁-C₁₀)heteroaryl, (C₁-C₁₀)heterocyclyl, (C₆-C₁₀)aryl-O—, (C₃-C₈)cycloalkyl-O—, (C₁-C₁₀)heteroaryl-O— and (C₁-C₁₀)heterocyclyl-O—; and R⁷ is selected from the group of suitable substituents such as hydrogen and (C₁-C₆)alkyl optionally substituted with one to three halogens, hydroxy, —CN, (C₁-C₆)alkoxy-, (C₂-C₆)alkenoxy, (C₁-C₆)alkyl-SO₂—, NH₂—, ((C₁-C₆)alkyl)ₙ-N—, ((C₂-C₆)alkenyl)ₙ-N—, ((C₂-C₆)alkynyl)ₙ-N—, NH₂(C═O)—, (C₁-C₆)alkyl-(C═O)N—, ((C₁-C₆)alkyl)ₙ-N—(C═O)—, (C₂-C₆)alkenyl-(C═O)N—, ((C₂-C₆)alkenyl)ₙ-N—(C═O)—, (C₂-C₆)alkynyl-(C═O)N—, ((C₂-C₆)alkynyl)ₙ-N—(C═O)—, (C₁-C₆)alkyl-(C═O)—, (C₂-C₆)alkenyl-(C═O)—, (C₂-C₆)alkynyl-(C═O)—, (C₃-C₁₀)cycloalkyl-(C═O)—, ((C₁-C₁₀)heterocyclyl-(C═O)—, (C₆-C₁₀)aryl-(C═O), (C₁-C₁₀)heteroaryl-(C═O), (C₁-C₆)alkyl-(C═O)O—, (C₂-C₆)alkenyl-(C═O)O—, (C₂-C₆)alkynyl-(C═O)O—, (C₁-C₆)alkyl-O(C═O)—, (C₂-C₆)alkenyl-O—(C═O)—, (C₂-C₆)alkynyl-O—(C═O)—, (C₃-C₁₀)cycloalkyl, (C₆-C₁₀)aryl, (C₁-C₁₀)heterocyclyl, and (C₁-C₁₀)heteroaryl;

wherein R⁴ and R⁷ may each be optionally substituted on any aliphatic or aromatic carbon atom by one to three suitable moieties, independently selected from the group consisting of halo, hydroxy, amino, —CN, (C₁-C₆)alkyl, (C₁-C₆)alkoxy, —CF₃, CF₃O—, (C₁-C₆)alkyl-NH—, [(C₁-C₆)alkyl]₂-N—, (C₁-C₆)alkyl-S—, (C₁-C₆)alkyl-(S═O)—, (C₁-C₆)alkyl-(SO₂)—, (C₁-C₆)alkyl-O—(C═O)—, formyl, (C₁-C₆)alkyl-(C═O)—, and (C₃-C₆)cycloalkyl;

R⁵ and R⁶ are each independently selected from the group consisting of hydrogen, (C₁-C₆)alkyl, HO—(C₂-C₆)alkyl and (C₃-C₈)cycloalkyl, or R⁵ and R⁶ may optionally be taken together with the nitrogen atom to which they are attached to form a 3 to 8 membered heterocycle;

n is an integer from zero to two; and m is an integer from one to two;

or the pharmaceutically acceptable salts or solvates or prodrugs thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

This invention also encompasses pharmaceutical compositions containing prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

This invention also encompasses compounds of formula I containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds. One example of a tautomeric structure is when R³ is a group of the formula

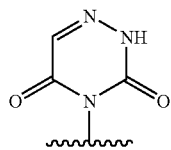

One skilled in the art will appreciate that this group can also be drawn as its tautomer

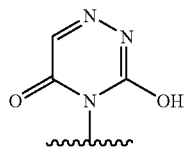

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

A "suitable substituent" is intended to mean a chemically and pharmaceutically acceptable functional group i.e., a moiety that does not negate the biological activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents. Further examples of suitable substituents include those recited in the definition of compounds of Formula I, including $R^1$ through $R^7$, as defined hereinabove.

As used herein, the term "spiro" refers to a connection between two groups, substituents etc., wherein the connection can be depicted according to the following formula

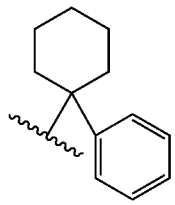

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_6)$alkyl, more preferred are $(C_1-C_4)$alkyl, and most preferred are methyl and ethyl.

As used herein, the term "cycloalkyl" refers to a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "halogen" includes fluoro, chloro, bromo or iodo or fluoride, chloride, bromide or iodide.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "oxo" is used herein to mean a double bonded oxygen (=O) radical wherein the bond partner is a carbon atom. Such a radical can also be thought as a carbonyl group.

As used herein, the term "$(C_1-C_4)$alkyl-$O_2$S—[$(C_1-C_4)$alkyl-N]-$" is used herein to mean a radical of the formula

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl.

The term "heterocyclic" as used herein refers to a cyclic group containing 1-9 carbon atoms and 1 to 4 hetero atoms selected from N, O, $S(O)_n$ or NR. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazinyl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Preferred heterocyclics include tetrahydrofuranyl, pyrrolidinyl, piperidinyl, piperazinyl and morpholinyl.

Nitrogen heteroatoms as used herein refers to N=, >N and —NH; wherein —N= refers to a nitrogen double bond; >N refers to a nitrogen containing two bond connections and —N refers to a nitrogen containing one bond.

"Embodiment" as used herein refers to specific groupings of compounds or uses into discrete subgenera. Such subgenera may be cognizable according to one particular substituent such as a specific $R^1$ or $R^3$ group. Other subgenera are cognizable according to combinations of various substituents, such as all compounds wherein $R^2$ is chloro and $R^1$ is $(C_1-C_4)$alkyl, optionally substituted by $(C_3-C_{10})$cycloalkyl. The phrase "in combination with each of the aforementioned embodiments" refers to combinations of the identified embodiment with each embodiment previously identified in the specification. Thus an embodiment of compounds wherein $R^1$ is $(C_1-C_4)$alkyl, optionally substituted by $(C_3-C_{10})$cycloalkyl "in combination with each of the aforementioned embodiments" refers to additional embodiments comprising combinations with each embodiment previously identified in the specification.

Thus, the invention provides compounds in which $R^1$ is $(C_1-C_4)$alkyl, optionally substituted by $(C_3-C_{10})$cycloalkyl; wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, $HO(C_1-C_6)$alkyl, $(C_1-C_6)$alkyl-NH (C=O)—, $NH_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The invention further provides compounds in which $R^1$ is $(C_1-C_4)$alkyl, optionally substituted by $(C_6-C_{10})$aryl; wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, $HO(C_1-C_6)$alkyl, $(C_1-C_6)$alkyl-NH (C=O)—, $NH_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Moreover, the invention contemplates compounds in which $R^2$ is halogen and $(C_1-C_6)$alkyl, and preferably compounds in which $R^2$ is chloro and methyl or ethyl.

In one embodiment of the invention, $R^3$ is a nitrogen linked $(C_1-C_{10})$heterocyclyl of formula (III), wherein $R^4$ is hydrogen and $R^7$ is independently selected from the group of suitable substituents such as hydrogen and $(C_1-C_6)$alkyl, wherein said $(C_1-C_6)$alkyl is optionally substituted with one to three substituents independently selected from halo, hydroxy, —CN, $(C_1-C_6)$alkoxy-, $(C_2-C_6)$alkenoxy, $(C_1-C_6)$alkyl-$SO_2$—, $NH_2$—, $((C_1-C_6)$alkyl$)_n$-N—, $((C_2-C_6)$alkenyl$)_n$-N—, $((C_2-C_6)$alkynyl$)_n$-N—, $NH_2$(C=O)—, $(C_1-C_6)$alkyl-(C=O)N—, $((C_1-C_6)$alkyl$)_n$-N—(C=O)—, $(C_2-C_6)$alkenyl-(C=O)N—, $((C_2-C_6)$alkenyl$)_n$-N—(C=O)—, $(C_2-C_6)$alkynyl-(C=O)N—, $((C_2-C_6)$alkynyl$)_n$-N—(C=O)—, $(C_1-C_6)$alkyl-(C=O)—, $(C_2-C_6)$alkenyl-(C=O)—, $(C_2-C_6)$alkynyl-(C=O)—, $(C_3-C_{10})$cycloalkyl-(C=O)—, $((C_1-C_{10})$heterocyclyl-(C=O)—, $(C_6-C_{10})$aryl-(C=O), $(C_1-C_{10})$heteroaryl-(C=O), $(C_1-C_6)$alkyl-(C=O)O—, $(C_2-C_6)$alkenyl-(C=O)O—, $(C_2-C_6)$alkynyl-(C=O)O—, $(C_1-C_6)$alkyl-O(C=O)—, $(C_2-C_6)$alkenyl-O—(C=O)—, $(C_2-C_6)$alkynyl-O—(C=O)—, $(C_3-C_{10})$cycloalkyl, $(C_6-C_{10})$aryl, $(C_1-C_{10})$heterocyclyl, and $(C_1-C_{10})$heteroaryl; wherein $R^7$ may optionally be substituted on any ring aliphatic or aromatic carbon atom by one to three suitable moieties, independently selected from the group consisting of halo, hydroxy, amino, —CN, $(C_1-C_4)$alkyl, $(C_1-C_4)$alkoxy, —$CF_3$, $CF_3$O—, $(C_1-C_4)$alkyl-NH—, $[(C_1-C_4)$alkyl$]_2$-N—, $(C_1-C_4)$alkyl-S—, $(C_1-C_4)$alkyl-(S=O)—, $(C_1-C_4)$alkyl-$(SO_2)$—, $(C_1-C_4)$alkyl-O—(C=O)—, formyl, $(C_1-C_4)$alkyl-(C=O)—, and $(C_3-C_6)$cycloalkyl.

Another embodiment of the invention are compounds in which $R^7$ is hydrogen.

A further embodiment of the invention are compounds in which $R^3$ is a nitrogen linked $(C_1-C_{10})$heterocyclyl of formula (III), wherein $R^4$ is hydrogen and $R^7$ is $(C_1-C_4)$alkyl optionally substituted with one to three substituents independently selected from halo-, hydroxy, —CN, $(C_1-C_4)$alkoxy-, $(C_2-C_4)$alkenoxy, and $(C_1-C_4)$alkyl-$SO_2$—. Preferably, $R^3$ is a nitrogen linked $(C_1-C_{10})$heterocyclyl of formula (II), wherein $R^4$ is hydrogen and $R^7$ is $(C_1-C_4)$alkyl optionally substituted with one to three substituents independently selected from halo-, hydroxy, —CN, or $(C_1-C_4)$alkoxy-.

Still further, the invention provides compounds in which $R^3$ is a nitrogen linked $(C_1-C_{10})$heterocyclyl of formula (III), wherein $R^4$ is hydrogen and $R^7$ is $(C_1-C_4)$alkyl optionally substituted with one to three substituents independently selected from $NH_2$—, $(C_1-C_4)$alkyl$)_n$-N—, $((C_2-C_4)$alkenyl$)_n$-N—, $((C_2-C_4)$alkynyl$)_n$-N—, $NH_2$(C=O)—, $(C_1-C_4)$alkyl-(C=O)N—, $((C_1-C_4)$alkyl$)_n$-N—(C=O)—, $(C_2-C_4)$alkenyl-(C=O)N—, $((C_2-C_4)$alkenyl$)_n$-N—(C=O)—, $(C_2-C_4)$alkynyl-(C=O)N—, and $((C_2-C_4)$alkynyl$)_n$-N—(C=O)—. Preferably, $R^3$ is a nitrogen linked $(C_1-C_{10})$heterocyclyl of formula (II), wherein $R^4$ is hydrogen and $R^7$ is ($C_1$-$C_4$)alkyl optionally substituted with one to three substituents independently selected from $NH_2$—, ($C_1$-$C_4$)alkyl)$_n$-N—, $NH_2$(C=O)—, ($C_1$-$C_4$)alkyl-(C=O)N—, and (($C_1$-$C_4$)alkyl)$_n$-N—(C=O)—.

The invention also provides compounds in which $R^3$ is a nitrogen linked ($C_1$-$C_{10}$)heterocyclyl of formula (III), wherein $R^4$ is hydrogen and $R^7$ is ($C_1$-$C_4$)alkyl optionally substituted with one to three substituents independently selected from ($C_1$-$C_4$)alkyl-(C=O)—, ($C_2$-$C_4$)alkenyl-(C=O)—, ($C_2$-$C_4$)alkynyl-(C=O)—, ($C_3$-$C_{10}$)cycloalkyl-(C=O)—, (($C_1$-$C_{10}$)heterocyclyl-(C=O)—, ($C_6$-$C_{10}$)aryl-(C=O), and ($C_1$-$C_{10}$)heteroaryl-(C=O), and preferably, $R^3$ is a nitrogen linked ($C_1$-$C_{10}$)heterocyclyl of formula (II), wherein $R^4$ is hydrogen and $R^7$ is ($C_1$-$C_4$)alkyl optionally substituted with one to three substituents independently selected from ($C_1$-$C_4$)alkyl-(C=O)—, ($C_3$-$C_{10}$)cycloalkyl-(C=O)—, (($C_1$-$C_{10}$)heterocyclyl-(C=O)—, ($C_6$-$C_{10}$)aryl-(C=O), and ($C_1$-$C_{10}$)heteroaryl-(C=O).

Another embodiment of the invention are compounds in which $R^3$ is a nitrogen linked ($C_1$-$C_{10}$)heterocyclyl of formula (III), wherein $R^4$ is hydrogen and $R^7$ is ($C_1$-$C_4$)alkyl optionally substituted with one to three substituents independently selected from ($C_1$-$C_4$)alkyl-(C=O)O—, ($C_2$-$C_4$)alkenyl-(C=O)O—, ($C_2$-$C_4$)alkynyl-(C=O)O—, ($C_1$-$C_4$)alkyl-O(C=O)—, ($C_2$-$C_4$)alkenyl-O—(C=O)—, and ($C_2$-$C_4$)alkynyl-O—(C=O)—. Preferably, $R^3$ is a nitrogen linked ($C_1$-$C_{10}$)heterocyclyl of formula (II), wherein $R^4$ is hydrogen and $R^7$ is ($C_1$-$C_4$)alkyl optionally substituted with one to three substituents independently selected from ($C_1$-$C_4$)alkyl-(C=O)O— and ($C_1$-$C_4$)alkyl-O(C=O)—.

Furthermore, the invention provides compounds in which $R^3$ is a nitrogen linked ($C_1$-$C_{10}$)heterocyclyl of formula (III), wherein $R^4$ is hydrogen and $R^7$ is ($C_1$-$C_4$)alkyl optionally substituted with one to three substituents independently selected from ($C_3$-$C_{10}$)cycloalkyl-, ($C_6$-$C_{10}$)aryl-, ($C_1$-$C_{10}$)heterocyclyl-, and ($C_1$-$C_{10}$)heteroaryl-.

The present invention also provides compounds of formula (I) wherein $R^3$ is a nitrogen linked ($C_1$-$C_{10}$)heterocyclyl of formula (IV):

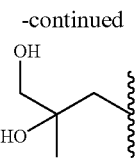

(IV)

and $R^7$ is selected from the group consisting of:

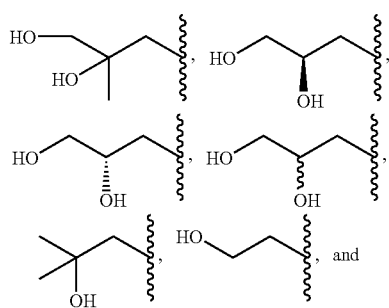

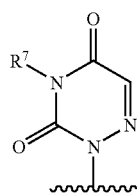

Also provided are compounds of formula (I) wherein $R^3$ is a nitrogen linked ($C_1$-$C_{10}$)heterocyclyl of formula (IV), and $R^7$ is

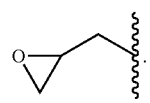

The present invention also contemplates compounds of formula (I) wherein $R^3$ is a nitrogen linked ($C_1$-$C_{10}$)heterocyclyl of formula (IV), and $R^7$ is selected from the group consisting of:

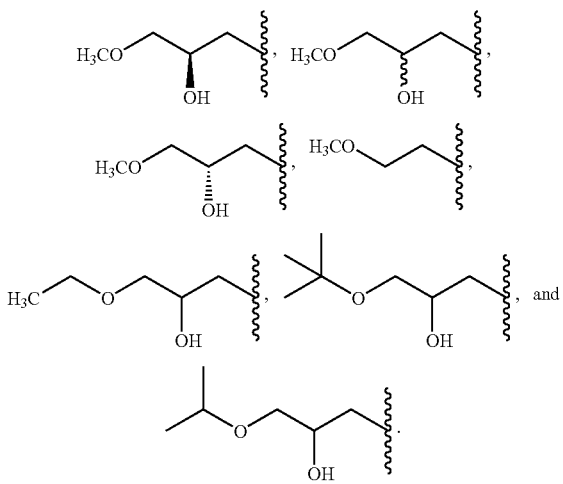

Also provided are compounds of formula (I) wherein $R^3$ is a nitrogen linked ($C_1$-$C_{10}$)heterocyclyl of formula (IV), and $R^7$ is

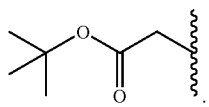

Also provided are compounds of formula (I) wherein $R^3$ is a nitrogen linked ($C_1$-$C_{10}$)heterocyclyl of formula (IV), and $R^7$ is selected from:

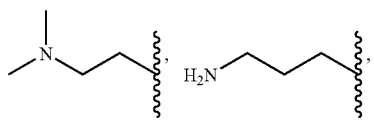

-continued

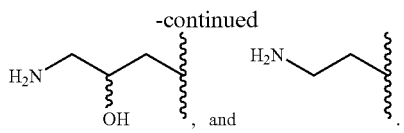

Finally, the invention further provides compounds of formula (I) wherein $R^3$ is a nitrogen linked $(C_1\text{-}C_{10})$heterocyclyl of formula (IV), and $R^7$ is selected from:

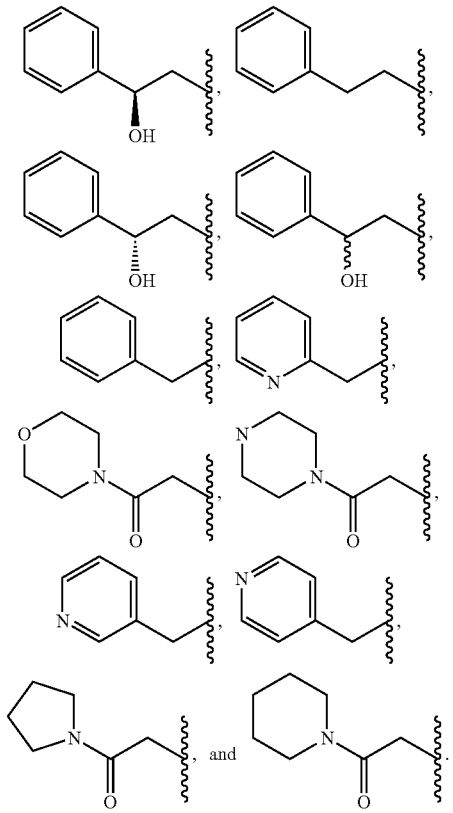

The present invention also provides compounds of formula (I) wherein $R^3$ is a nitrogen linked $(C_1\text{-}C_{10})$heterocyclyl of formula (IV), $R^7$ is selected from the group consisting of:

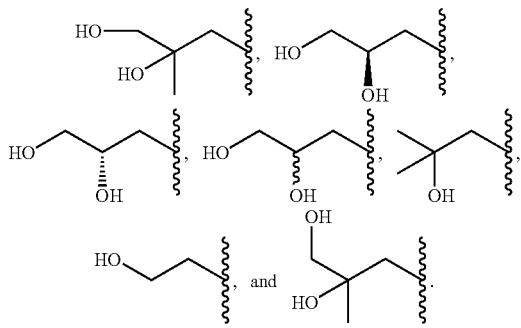

and $R^1$ is selected from the group consisting of $(C_1\text{-}C_4)$alkyl, optionally substituted by $(C_3\text{-}C_{10})$cycloalkyl, wherein said $(C_1\text{-}C_4)$alkyl or $(C_3\text{-}C_{10})$cycloalkyl are optionally substituted by one to three suitable moieties independently selected from the group consisting of hydroxy, halogen, CN—, $(C_1\text{-}C_6)$alkyl, HO$(C_1\text{-}C_6)$alkyl, $(C_1\text{-}C_6)$alkyl-NH(C=O)—, NH$_2$(C=O)—, $(C_1\text{-}C_6)$alkoxy, or $(C_3\text{-}C_{10})$cycloalkyl, wherein said $(C_3\text{-}C_{10})$cycloalkyl is optionally substituted by one or more moieties selected from halogen, or $(C_1\text{-}C_6)$alkyl-.

The present invention also provides compounds of formula (I) wherein $R^3$ is a nitrogen linked $(C_1\text{-}C_{10})$heterocyclyl of formula (IV), $R^7$ is selected from the group consisting of:

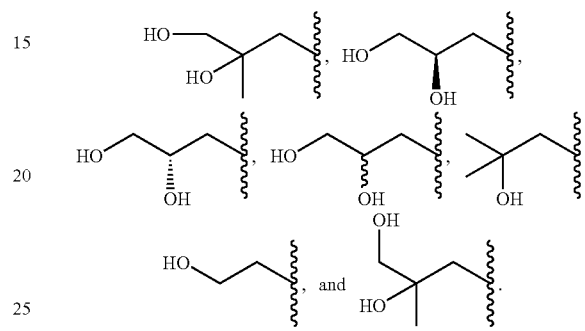

and $R^1$ is selected from the group consisting of $(C_1\text{-}C_4)$alkyl, optionally substituted by $(C_6\text{-}C_{10})$aryl, wherein said $(C_1\text{-}C_4)$alkyl or $(C_6\text{-}C_{10})$aryl are optionally substituted by one to three suitable moieties independently selected from the group consisting of hydroxy, halogen, CN—, $(C_1\text{-}C_6)$alkyl, HO$(C_1$-$C_6)$alkyl, $(C_1\text{-}C_6)$alkyl-NH(C=O)—, NH$_2$(C=O)—, $(C_1$-$C_6)$alkoxy, or $(C_3\text{-}C_{10})$cycloalkyl, wherein said $(C_3\text{-}C_{10})$cycloalkyl is optionally substituted by one or more moieties selected from halogen, or $(C_1\text{-}C_6)$alkyl-.

Also provided are compounds of formula (I) wherein $R^3$ is a nitrogen linked $(C_1\text{-}C_{10})$heterocyclyl of formula (IV), $R^7$ is

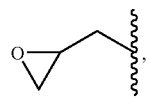

and $R^1$ is selected from the group consisting of $(C_1\text{-}C_4)$alkyl, optionally substituted by $(C_3\text{-}C_{10})$cycloalkyl, wherein said $(C_1\text{-}C_4)$alkyl or $(C_3\text{-}C_{10})$cycloalkyl are optionally substituted by one to three suitable moieties independently selected from the group consisting of hydroxy, halogen, CN—, $(C_1\text{-}C_6)$alkyl, HO$(C_1\text{-}C_6)$alkyl, $(C_1\text{-}C_6)$alkyl-NH(C=O)—, NH$_2$(C=O)—, $(C_1\text{-}C_6)$alkoxy, or $(C_3\text{-}C_{10})$cycloalkyl, wherein said $(C_3\text{-}C_{10})$cycloalkyl is optionally substituted by one or more moieties selected from halogen, or $(C_1\text{-}C_6)$alkyl-.

Also provided are compounds of formula (I) wherein $R^3$ is a nitrogen linked $(C_1\text{-}C_{10})$heterocyclyl of formula (IV), $R^7$ is

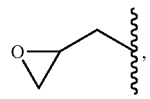

and $R^1$ is selected from the group consisting of $(C_1-C_4)$alkyl, optionally substituted by $(C_6-C_{10})$aryl, wherein said $(C_1-C_4)$ alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The present invention also contemplates compounds of formula (I) wherein $R^3$ is a nitrogen linked $(C_1-C_{10})$heterocyclyl of formula (IV), $R^7$ is selected from the group consisting of:

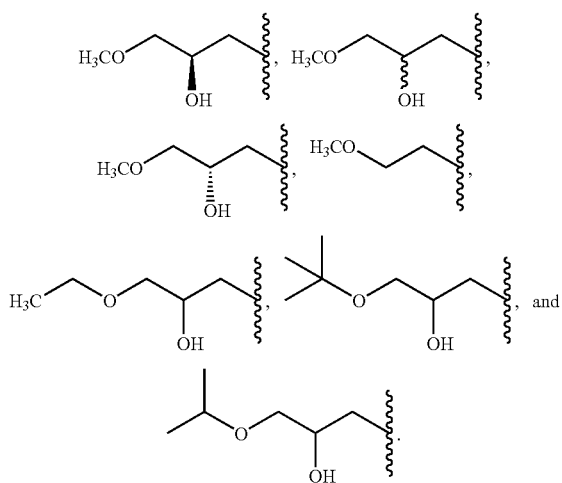

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The present invention also contemplates compounds of formula (I) wherein $R^3$ is a nitrogen linked $(C_1-C_{10})$heterocyclyl of formula (IV), $R^7$ is selected from the group consisting of:

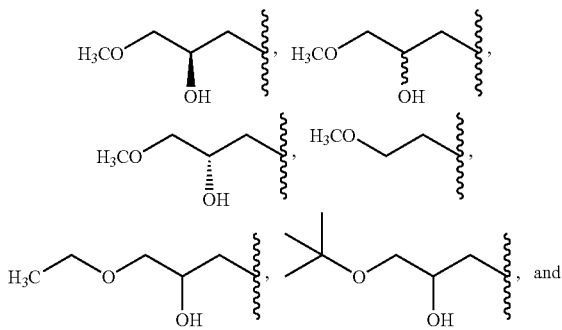

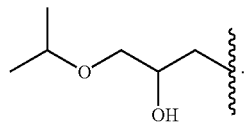

and $R^1$ is selected from the group consisting of $(C_1-C_4)$alkyl, optionally substituted by $(C_6-C_{10})$aryl, wherein said $(C_1-C_4)$ alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is

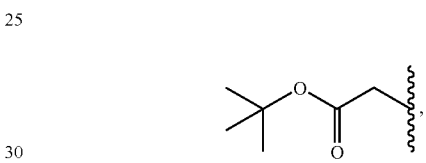

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$ alkyl, HO$(C_1-C_6)$alkyl, $(C_1-C_6)$alkyl-NH(C=O)—, NH$_2$ (C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is

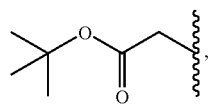

and $R^1$ is selected from the group consisting of $(C_1-C_4)$alkyl, optionally substituted by $(C_6-C_{10})$aryl, wherein said $(C_1-C_4)$ alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is selected from:

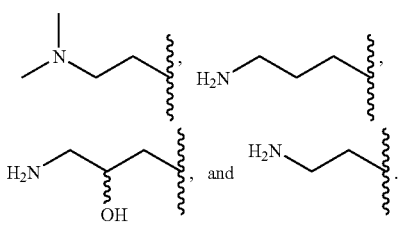

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, $NH_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is selected from:

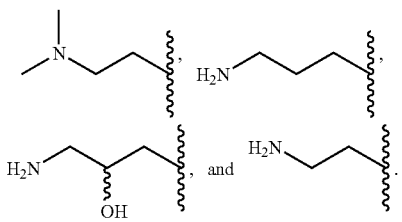

and $R^1$ is selected from the group consisting of $(C_1-C_4)$alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, $NH_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The invention further provides compounds of formula (I) wherein $R^3$ is a nitrogen linked $(C_1-C_{10})$heterocyclyl of formula (IV), $R^7$ is selected from:

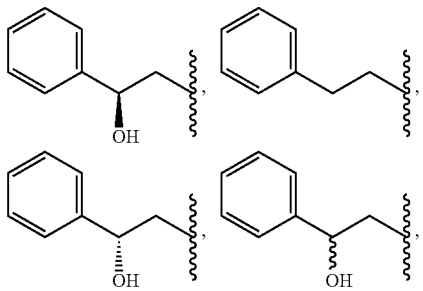

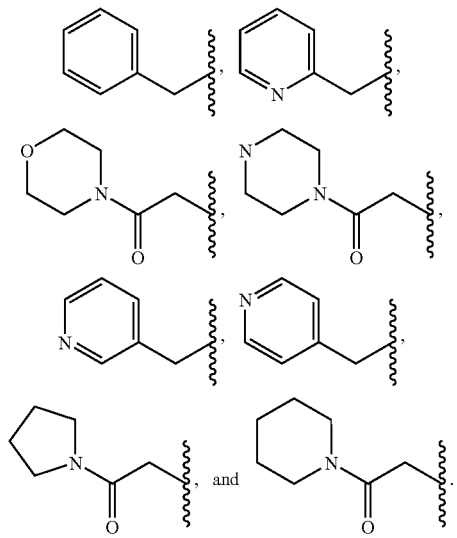

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, $NH_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Finally, the invention further provides compounds of formula (I) wherein $R^3$ is a nitrogen linked $(C_1-C_{10})$heterocyclyl of formula (IV), $R^7$ is selected from:

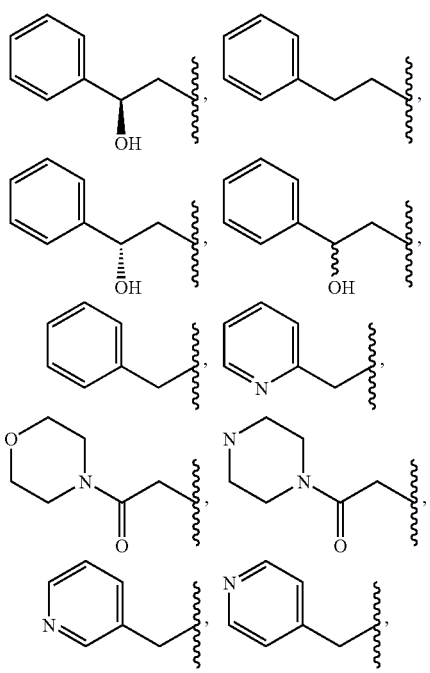

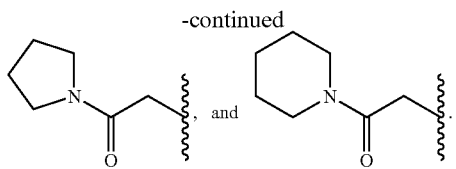

and $R^1$ is selected from the group consisting of $(C_1-C_4)$alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The present invention also provides compounds of formula (I) wherein $R^3$ is a nitrogen linked $(C_1-C_{10})$heterocyclyl of formula (IV), $R^7$ is selected from the group consisting of:

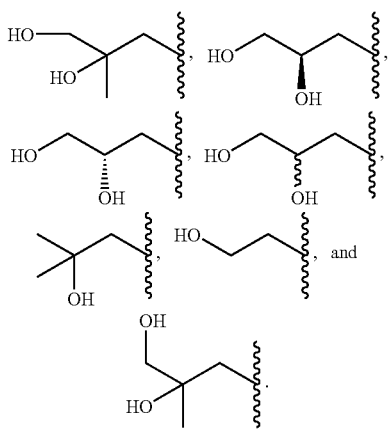

$R^2$ is chloro, methyl or ethyl;

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The present invention also provides compounds of formula (I) wherein $R^3$ is a nitrogen linked $(C_1-C_{10})$heterocyclyl of formula (IV), $R^7$ is selected from the group consisting of:

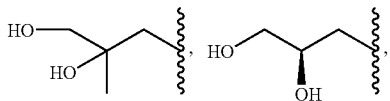

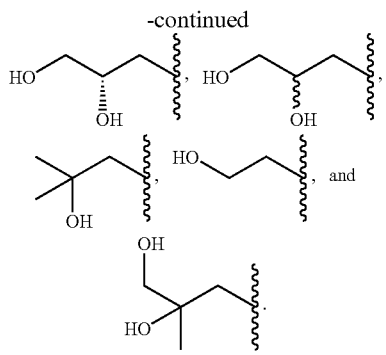

$R^2$ is chloro, methyl or ethyl;

and $R^1$ is selected from the group consisting of $(C_1-C_4)$alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is

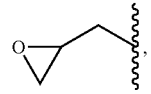

$R^2$ is chloro, methyl or ethyl;

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is

$R^2$ is chloro, methyl or ethyl;

and $R^1$ is selected from the group consisting of $(C_1-C_4)$alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The present invention also contemplates compounds of formula (I) wherein $R^3$ is a nitrogen linked $(C_1-C_{10})$heterocyclyl of formula (IV), $R^7$ is selected from the group consisting of:

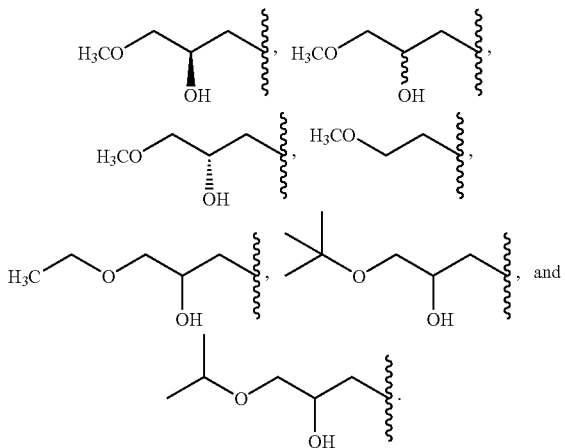

$R^2$ is chloro, methyl or ethyl;

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The present invention also contemplates compounds of formula (I) wherein $R^3$ is a nitrogen linked $(C_1-C_{10})$heterocyclyl of formula (IV), $R^7$ is selected from the group consisting of:

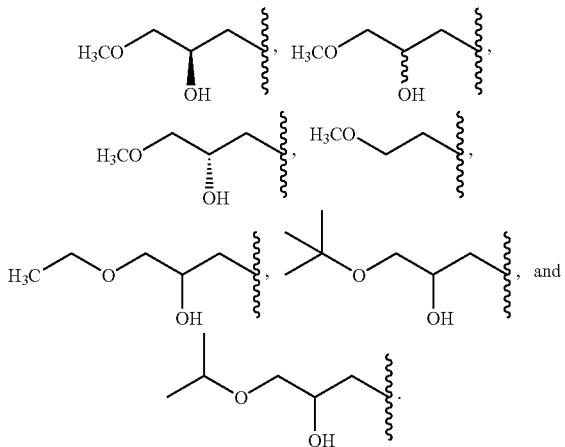

$R^2$ is chloro, methyl or ethyl;

and $R^1$ is selected from the group consisting of $(C_1-C_4)$alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is

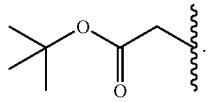

$R^2$ is chloro, methyl or ethyl;

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is

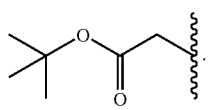

$R^2$ is chloro, methyl or ethyl;

and $R^1$ is selected from the group consisting of $(C_1-C_4)$alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is selected from:

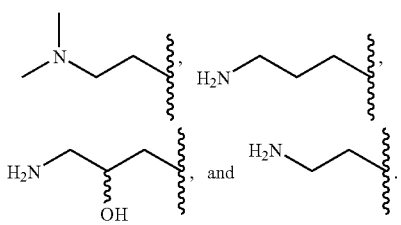

$R^2$ is chloro, methyl or ethyl;

and $R^1$ is selected from the group consisting of $(C_1-C_4)$alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Also provided are compounds of formula (I) wherein $R^3$ is a nitrogen linked $(C_1-C_{10})$heterocyclyl of formula (IV), $R^7$ is selected from:

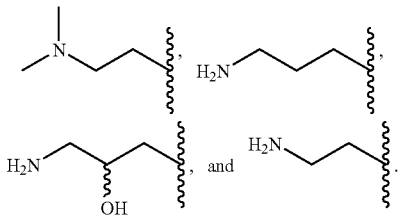

$R^2$ is chloro, methyl or ethyl;

and $R^1$ is selected from the group consisting of $(C_1-C_4)$ alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

The invention further provides compounds of formula (I) wherein $R^3$ is a nitrogen linked $(C_1-C_{10})$heterocyclyl of formula (IV), $R^7$ is selected from:

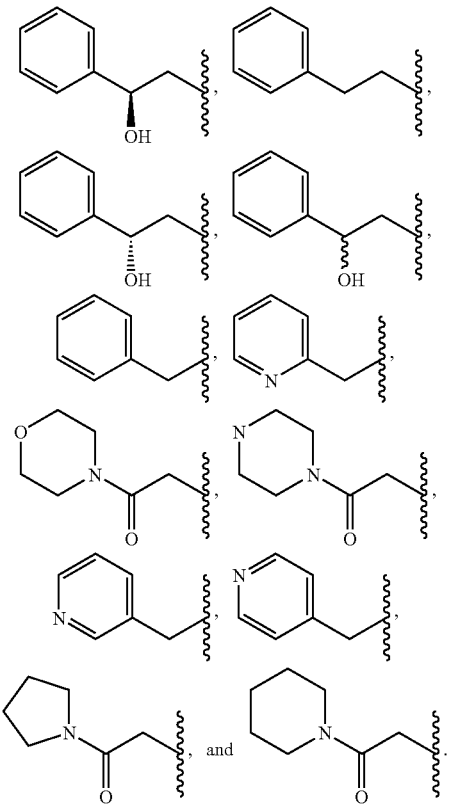

$R^2$ is chloro, methyl or ethyl;

and $R^1$ is selected from the group consisting of $(C_1-C_4)$ alkyl, optionally substituted by $(C_3-C_{10})$cycloalkyl, wherein said $(C_1-C_4)$alkyl or $(C_3-C_{10})$cycloalkyl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Finally, the invention further provides compounds of formula (I) wherein $R^3$ is a nitrogen linked $(C_1-C_{10})$heterocyclyl of formula (IV), $R^7$ is selected from:

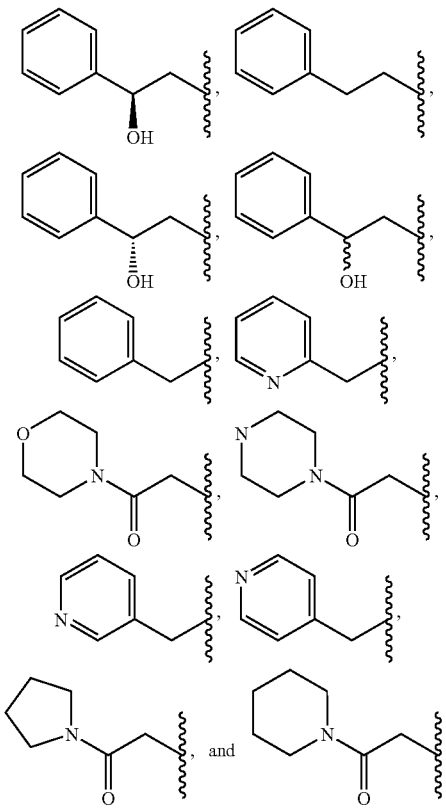

$R^2$ is chloro, methyl or ethyl;

and $R^1$ is selected from the group consisting of $(C_1-C_4)$ alkyl, optionally substituted by $(C_6-C_{10})$aryl, wherein said $(C_1-C_4)$alkyl or $(C_6-C_{10})$aryl are optionally substituted by one to three suitable moieties independently selected from the group consisting of hydroxy, halogen, CN—, $(C_1-C_6)$alkyl, HO$(C_1-C_6)$alkyl, $(C_1-C_6)$alkyl-NH(C=O)—, NH$_2$(C=O)—, $(C_1-C_6)$alkoxy, or $(C_3-C_{10})$cycloalkyl, wherein said $(C_3-C_{10})$cycloalkyl is optionally substituted by one or more moieties selected from halogen, or $(C_1-C_6)$alkyl-.

Examples of other compounds of formula I are the following:
  2-Chloro-N-(1-hydroxy-cycloheptylmethyl)-5-[4-(2-methanesulfonylamino-ethyl)-3,5-dioxo-4,5-dihydro-3H-[1,2,4]triazin-2-yl]-benzamide;
  2-Chloro-5-[4-(2-formylamino-ethyl)-3,5-dioxo-4,5-dihydro-3H-[1,2,4]triazin-2-yl]-N-(1-hydroxy-cycloheptylmethyl)-benzamide;

5-[4-(1-Amino-cyclopropylmethyl)-3,5-dioxo-4,5-dihydro-3H-[1,2,4]triazin-2-yl]-2-chloro-N-(1-hydroxy-cycloheptylmethyl)-benzamide;

2-Chloro-N-(1-hydroxy-cycloheptylmethyl)-5-[4-(1-hydroxy-cyclopropylmethyl)-3,5-dioxo-4,5-dihydro-3H-[1,2,4]triazin-2-yl]-benzamide;

5-[4-(2-Amino-2-methyl-propyl)-3,5-dioxo-4,5-dihydro-3H-[1,2,4]triazin-2-yl]-2-chloro-N-(1-hydroxy-cycloheptylmethyl)-benzamide;

2-Chloro-5-[4-(3-difluoromethoxy-2-hydroxy-propyl)-3,5-dioxo-4,5-dihydro-3H-[1,2,4]triazin-2-yl]-N-(t-hydroxy-cycloheptylmethyl)-benzamide;

N-(1-Hydroxy-cycloheptylmethyl)-5-[4-(2-hydroxy-3-methoxy-propyl)-3,5-dioxo-4,5-dihydro-3H-[1,2,4]triazin-2-yl]-2-methyl-benzamide;

5-[4-(2-Hydroxy-3-methoxy-propyl)-3,5-dioxo-4,5-dihydro-3H-[1,2,4]triazin-2-yl]-N-(1-hydroxymethyl-cycloheptylmethyl)-2-methyl-benzamide;

N-(1-Hydroxy-cyclohexylmethyl)-5-[4-(2-hydroxy-3-methoxy-propyl)-3,5-dioxo-4,5-dihydro-3H-[1,2,4]triazin-2-yl]-2-methyl-benzamide;

1-({2-Chloro-5-[4-(2-hydroxy-3-methoxy-propyl)-3,5-dioxo-4,5-dihydro-3H-[1,2,4]triazin-2-yl]-benzoylamino}-methyl)-cycloheptanecarboxylic acid amide;

2-Chloro-N-[2-(2-chloro-phenyl)-ethyl]-5-[4-(2,3-dihydroxy-propyl)-3,5-dioxo-4,5-dihydro-3H-[1,2,4]triazin-2-yl]-benzamide;

2-Chloro-5-[4-(2,3-dihydroxy-propyl)-3,5-dioxo-4,5-dihydro-3H-[1,2,4]triazin-2-yl]-N-(1-hydroxymethyl-cycloheptylmethyl)-benzamide;

1-({2-Chloro-5-[4-(2,3-dihydroxy-propyl)-3,5-dioxo-4,5-dihydro-3H-[1,2,4]triazin-2-yl]-benzoylamino}-methyl)-cycloheptanecarboxylic acid amide;

2-Chloro-5-[4-(2,3-dihydroxy-propyl)-3,5-dioxo-4,5-dihydro-3H-[1,2,4]triazin-2-yl]-N-phenethyl-benzamide;

2-Chloro-5-[4-(2,3-dihydroxy-propyl)-3,5-dioxo-4,5-dihydro-3H-[1,2,4]triazin-2-yl]-N-(1-hydroxy-cyclohexylmethyl)-benzamide;

2-Chloro-5-[4-(2,3-dihydroxy-propyl)-3,5-dioxo-4,5-dihydro-3H-[1,2,4]triazin-2-yl]-N-(1-hydroxy-cyclopentylmethyl)-benzamide;

2-Chloro-5-[4-(2,3-dihydroxy-propyl)-3,5-dioxo-4,5-dihydro-3H-[1,2,4]triazin-2-yl]-N-(1-hydroxy-cyclobutylmethyl)-benzamide;

2-Chloro-N-(1-hydroxy-cycloheptylmethyl)-5-[4-(2-hydroxy-3-trifluoromethoxy-propyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-propyl)-3,5-dioxo-4,5-dihydro-3H-[1,2,4]triazin-2-yl]-benzamide;

2-Chloro-5-[4-(2-hydroxy-butyl)-3,5-dioxo-4,5-dihydro-3H-[1,2,4]triazin-2-yl]-N-(1-hydroxy-cycloheptylmethyl)-benzamide;

5-[4-(2-Amino-propyl)-3,5-dioxo-4,5-dihydro-3H-[1,2,4]triazin-2-yl]-2-chloro-N-(1-hydroxy-cycloheptylmethyl)-benzamide;

2-Chloro-5-[3,5-dioxo-4-(2-oxo-propyl)-4,5-dihydro-3H-[1,2,4]triazin-2-yl]-N-(1-hydroxy-cycloheptylmethyl)-benzamide;

2-Chloro-5-[3,5-dioxo-4-(2-oxo-ethyl)-4,5-dihydro-3H-[1,2,4]triazin-2-yl]-N-(1-hydroxy-cycloheptylmethyl)-benzamide;

2-Chloro-5-[3,5-dioxo-4-(2-trifluoromethoxy-ethyl)-4,5-dihydro-3H-[1,2,4]triazin-2-yl]-N-(1-hydroxy-cycloheptylmethyl)-benzamide;

2-Chloro-5-[4-(1-hydroxy-cyclobutyl ethyl)-3,5-dioxo-4,5-dihydro-3H-[1,2,4]triazin-2-yl]-N-(1-hydroxy-cycloheptylmethyl)-benzamide;

2-Chloro-N-(1-hydroxy-cycloheptylmethyl)-5-[4-(2-hydroxy-2-pyridin-4-yl-ethyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-2-pyridin-3-yl-ethyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-2-pyridin-2-yl-ethyl)-3,5-dioxo-4,5-dihydro-3H-[1,2,4]triazin-2-yl]-benzamide;

2-Chloro-N-(1-hydroxy-cycloheptylmethyl)-5-[4-(4-hydroxy-tetrahydro-pyran-4-ylmethyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-2-thiophen-2-yl-ethyl)-3,5-dioxo-4,5-dihydro-3H-[1,2,4]triazin-2-yl]-benzamide;

2-Chloro-5-[4-(2-furan-2-yl-2-hydroxy-ethyl)-3,5-dioxo-4,5-dihydro-3H-[1,2,4]triazin-2-yl]-N-(1-hydroxy-cycloheptylmethyl)-benzamide;

5-(4-Carbamoylmethyl-3,5-dioxo-4,5-dihydro-3H-[1,2,4]triazin-2-yl)-2-chloro-N-[2-(2-chloro-phenyl)-ethyl]-benzamide;

2-Chloro-N-[2-(2-chloro-phenyl)-ethyl]-5-[4-(2-methoxy-ethyl)-3,5-dioxo-4,5-dihydro-3H-[1,2,4]triazin-2-yl]-benzamide;

5-[4-(2-Carbamoyl-ethyl)-3,5-dioxo-4,5-dihydro-3H-[1,2,4]triazin-2-yl]-2-chloro-N-[2-(2-chloro-phenyl)-ethyl]-benzamide;

2-Chloro-N-[2-(2-chloro-phenyl)-ethyl]-5-[4-(2-hydroxy-ethyl)-3,5-dioxo-4,5-dihydro-3H-[1,2,4]triazin-2-yl]-benzamide;

2-Chloro-N-[2-(2-chloro-phenyl)-ethyl]-5-[4-(3-hydroxy-propyl)-3,5-dioxo-4,5-dihydro-3H-[1,2,4]triazin-2-yl]-benzamide;

5-(4-Carbamoylmethyl-3,5-dioxo-4,5-dihydro-3H-[1,2,4]triazin-2-yl)-2-chloro-N-(1-hydroxy-cycloheptylmethyl)-benzamide;

2-Chloro-N-(1-hydroxy-cycloheptylmethyl)-5-[4-(2-hydroxy-ethyl)-3,5-dioxo-4,5-dihydro-3H-[1,2,4]triazin-2-yl]-benzamide;

2-Chloro-N-(1-hydroxy-cycloheptylmethyl)-5-[4-(2-methoxy-ethyl)-3,5-dioxo-4,5-dihydro-3H-[1,2,4]triazin-2-yl]-benzamide;

2-Chloro-5-[4-(2-dimethylamino-ethyl)-3,5-dioxo-4,5-dihydro-3H-[1,2,4]triazin-2-yl]-N-(1-hydroxy-cycloheptylmethyl)-benzamide;

2-Chloro-5-(4-cyanomethyl-3,5-dioxo-4,5-dihydro-3H-[1,2,4]triazin-2-yl)-N-(1-hydroxy-cycloheptylmethyl)-benzamide;

2-Chloro-N-(1-hydroxy-cycloheptylmethyl)-5-[4-(3-hydroxy-propyl)-3,5-dioxo-4,5-dihydro-3H-[1,2,4]triazin-2-yl]-benzamide;

5-[4-(2-Amino-ethyl)-3,5-dioxo-4,5-dihydro-3H-[1,2,4]triazin-2-yl]-2-chloro-N-(1-hydroxy-cycloheptylmethyl)-benzamide;

2-Chloro-N-(1-hydroxy-cycloheptylmethyl)-5-(4-oxiranylmethyl-3,5-dioxo-4,5-dihydro-3H-[1,2,4]triazin-2-yl)-benzamide;

5-[4-(2-Acetylamino-ethyl)-3,5-dioxo-4,5-dihydro-3H-[1,2,4]triazin-2-yl]-2-chloro-N-(1-hydroxy-cycloheptylmethyl)-benzamide;

2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide;

2-Chloro-5-(3,5-dioxo-4-phenethyl-4,5-dihydro-3H-[1,2,4]triazin-2-yl)-N-(1-hydroxy-cycloheptylmethyl)-benzamide;
5-(4-Benzyl-3,5-dioxo-4,5-dihydro-3H-[1,2,4]triazin-2-yl)-2-chloro-N-(1-hydroxy-cycloheptylmethyl)-benzamide;
2-Chloro-5-[4-(2-cyano-ethyl)-3,5-dioxo-4,5-dihydro-3H-[1,2,4]triazin-2-yl]-N-(1-hydroxy-cycloheptylmethyl)-benzamide;
2-Chloro-5-(3,5-dioxo-4-pyridin-2-ylmethyl-4,5-dihydro-3H-[1,2,4]triazin-2-yl)-N-(1-hydroxy-cycloheptylmethyl)-benzamide;
2-Chloro-5-(3,5-dioxo-4-pyridin-3-ylmethyl-4,5-dihydro-3H-[1,2,4]triazin-2-yl)-N-(1-hydroxy-cycloheptylmethyl)-benzamide;
2-Chloro-5-(3,5-dioxo-4-pyridin-4-ylmethyl-4,5-dihydro-3H-[1,2,4]triazin-2-yl)-N-(1-hydroxy-cycloheptylmethyl)-benzamide;
5-[4-(2-Carbamoyl-ethyl)-3,5-dioxo-4,5-dihydro-3H-[1,2,4]triazin-2-yl]-2-chloro-N-(1-hydroxy-cycloheptylmethyl)-benzamide;
N-(1-Hydroxy-cycloheptylmethyl)-5-[4-(2-hydroxy-ethyl)-3,5-dioxo-4,5-dihydro-3H-[1,2,4]triazin-2-yl]-2-methyl-benzamide;
5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide;
5-[4-(2-Carbamoyl-ethyl)-3,5-dioxo-4,5-dihydro-3H-[1,2,4]triazin-2-yl]-N-(1-hydroxy-cycloheptylmethyl)-2-methyl-benzamide;
5-[4-(3-Amino-propyl)-3,5-dioxo-4,5-dihydro-3H-[1,2,4]triazin-2-yl]-2-chloro-N-(1-hydroxy-cycloheptylmethyl)-benzamide;
2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide;
(2-{4-Chloro-3-[2-(2-chloro-phenyl)-ethylcarbamoyl]-phenyl}-3,5-dioxo-2,5-dihydro-3H-[1,2,4]triazin-4-yl)-acetic acid tert-butyl ester;
2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide;
5-(4-Carbamoylmethyl-3,5-dioxo-4,5-dihydro-3H-[1,2,4]triazin-2-yl)-2-chloro-N-(1-cyano-cycloheptylmethyl)-benzamide;
N-Adamantan-1-ylmethyl-5-(4-carbamoylmethyl-3,5-dioxo-4,5-dihydro-3H-[1,2,4]triazin-2-yl)-2-chloro-benzamide;
5-(4-Carbamoylmethyl-3,5-dioxo-4,5-dihydro-3H-[1,2,4]triazin-2-yl)-2-chloro-N-(4,4-difluoro-1-phenyl-cyclohexylmethyl)-benzamide;
5-(4-Carbamoylmethyl-3,5-dioxo-4,5-dihydro-3H-[1,2,4]triazin-2-yl)-2-chloro-N-(1-p-tolyl-cyclohexylmethyl)-benzamide;
5-(4-Carbamoylmethyl-3,5-dioxo-4,5-dihydro-3H-[1,2,4]triazin-2-yl)-2-chloro-N-(1-hydroxy-cyclohexylmethyl)-benzamide;
2-Chloro-N-(1-hydroxy-cyclohexylmethyl)-5-[4-(2-hydroxy-ethyl)-3,5-dioxo-4,5-dihydro-3H-[1,2,4]triazin-2-yl]-benzamide;
2-Chloro-N-(1-hydroxy-3,3-dimethyl-cyclohexylmethyl)-5-[4-(2-hydroxy-ethyl)-3,5-dioxo-4,5-dihydro-3H-[1,2,4]triazin-2-yl]-benzamide;
2-Chloro-N-(1-hydroxy-cyclooctylmethyl)-5-[4-(2-hydroxy-ethyl)-3,5-dioxo-4,5-dihydro-3H-[1,2,4]triazin-2-yl]-benzamide;
2-Chloro-5-[4-(2,3-dihydroxy-propyl)-3,5-dioxo-4,5-dihydro-3H-[1,2,4]triazin-2-yl]-N-(1-hydroxy-cyclohexylmethyl)-benzamide;
5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide;
5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide;
5-(4-Carbamoylmethyl-3,5-dioxo-4,5-dihydro-3H-[1,2,4]triazin-2-yl)-2-chloro-N-(1-hydroxy-cyclooctylmethyl)-benzamide;
2-Chloro-N-(2-hydroxy-cycloheptylmethyl)-5-[4-(2-hydroxy-ethyl)-3,5-dioxo-4,5-dihydro-3H-[1,2,4]triazin-2-yl]-benzamide;
5-[4-(3-Amino-2-hydroxy-propyl)-3,5-dioxo-4,5-dihydro-3H-[1,2,4]triazin-2-yl]-2-chloro-N-(1-hydroxy-cycloheptylmethyl)-benzamide;
2-Chloro-N-(1-hydroxy-cycloheptylmethyl)-5-(4-methylcarbamoylmethyl-3,5-dioxo-4,5-dihydro-3H-[1,2,4]triazin-2-yl)-benzamide;
2-Chloro-N-[2-(2-chloro-phenyl)-ethyl]-5-(4-dimethylcarbamoylmethyl-3,5-dioxo-4,5-dihydro-3H-[1,2,4]triazin-2-yl)-benzamide;
2-Chloro-N-[2-(2-chloro-phenyl)-ethyl]-5-[4-(2-morpholin-4-yl-2-oxo-ethyl)-3,5-dioxo-4,5-dihydro-3H-[1,2,4]triazin-2-yl]-benzamide;
2-Chloro-N-[2-(2-chloro-phenyl)-ethyl]-5-[3,5-dioxo-4-(2-oxo-2-pyrrolidin-yl-ethyl)-4,5-dihydro-3H-[1,2,4]triazin-2-yl]-benzamide;
2-Chloro-N-[2-(2-chloro-phenyl)-ethyl]-5-[4-(2-methylcarbamoyl-ethyl)-3,5-dioxo-4,5-dihydro-3H-[1,2,4]triazin-2-yl]-benzamide;
2-Chloro-N-[2-(2-chloro-phenyl)-ethyl]-5-[4-(2-dimethylcarbamoyl-ethyl)-3,5-dioxo-4,5-dihydro-3H-[1,2,4]triazin-2-yl]-benzamide;
2-Chloro-N-[2-(2-chloro-phenyl)-ethyl]-5-[3,5-dioxo-4-(2-oxo-2-piperazin-1-yl-ethyl)-4,5-dihydro-3H-[1,2,4]triazin-2-yl]-benzamide;
2-Chloro-5-(4-dimethylcarbamoylmethyl-3,5-dioxo-4,5-dihydro-3H-[1,2,4]triazin-2-yl)-N-(1-hydroxy-cycloheptylmethyl)-benzamide;
2-Chloro-5-(4-ethylcarbamoylmethyl-3,5-dioxo-4,5-dihydro-3H-[1,2,4]triazin-2-yl)-N-(1-hydroxy-cycloheptylmethyl)-benzamide;
2-Chloro-5-[3,5-dioxo-4-(2-oxo-2-piperidin-1-yl-ethyl)-4,5-dihydro-3H-[1,2,4]triazin-2-yl]-N-(1-hydroxy-cycloheptylmethyl)-benzamide;
2-Chloro-N-(1-hydroxy-cycloheptylmethyl)-5-[4-(2-morpholin-4-yl-2-oxo-ethyl)-3,5-dioxo-4,5-dihydro-3H-[1,2,4]triazin-2-yl]-benzamide;
2-Chloro-N-(1-hydroxy-cycloheptylmethyl)-5-[4-(isopropylcarbamoyl-methyl)-3,5-dioxo-4,5-dihydro-3H-[1,2,4]triazin-2-yl]-benzamide;
2-Chloro-5-[3,5-dioxo-4-(2-oxo-2-pyrrolidin-1-yl-ethyl)-4,5-dihydro-3H-[1,2,4]triazin-2-yl]-N-(1-hydroxy-cycloheptylmethyl)-benzamide;
2-Chloro-5-{4-[(cyclopropylmethyl-carbamoyl)-methyl]-3,5-dioxo-4,5-dihydro-3H-[1,2,4]triazin-2-yl}-N-(1-hydroxy-cycloheptylmethyl)-benzamide;
5-(4-Dimethylcarbamoylmethyl-3,5-dioxo-4,5-dihydro-3H-[1,2,4]triazin-2-yl)-N-(1-hydroxy-cycloheptylmethyl)-2-methyl-benzamide;
2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide;

2-Chloro-5-[4-(2,3-dihydroxy-2-methyl-propyl)-3,5-di-oxo-4,5-dihydro-3H-[1,2,4]triazin-2-yl]-N-(1-hydroxy-cycloheptylmethyl)-benzamide;

2-Chloro-N-(1-hydroxy-cycloheptylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cyclohexylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cyclooctylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cyclohexylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cyclopentylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cyclobutylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cyclobutylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide;

2-Chloro-5-[4-(2-hydroxy-3-methoxy-propyl)-3,5-dioxo-4,5-dihydro-3H-[1,2,4]triazin-2-yl]-N-(1-hydroxymethyl-cycloheptylmethyl)-benzamide;

2-Chloro-N-(1-hydroxymethyl-cycloheptylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-2-phenyl-ethyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-2-phenyl-ethyl)-3,5-dioxo-4,5-dihydro-3H-[1,2,4]triazin-2-yl]-benzamide;

2-Chloro-5-[4-(3-ethoxy-2-hydroxy-propyl)-3,5-dioxo-4,5-dihydro-3H-[1,2,4]triazin-2-yl]-N-(1-hydroxy-cycloheptylmethyl)-benzamide;

2-Chloro-N-(1-hydroxy-cycloheptylmethyl)-5-[4-(2-hydroxy-3-isopropoxy-propyl)-3,5-dioxo-4,5-dihydro-3H-[1,2,4]triazin-2-yl]-benzamide;

5-[4-(3-tert-Butoxy-2-hydroxy-propyl)-3,5-dioxo-4,5-dihydro-3H-[1,2,4]triazin-2-yl]-2-chloro-N-(1-hydroxy-cycloheptylmethyl)-benzamide;

2-Chloro-N-[2-(2-chloro-phenyl)-ethyl]-5-[4-(2-hydroxy-3-methoxy-propyl)-3,5-dioxo-4,5-dihydro-3H-[1,2,4]triazin-2-yl]-benzamide;

2-Chloro-5-[3,5-dioxo-4-(3,3,3-trifluoro-2-hydroxy-propyl)-4,5-dihydro-3H-[1,2,4]triazin-2-yl]-N-(1-hydroxy-cycloheptylmethyl)-benzamide;

2-Chloro-N-(1-hydroxy-cycloheptylmethyl)-5-[4-(2-hydroxy-3,3-dimethyl-butyl)-3,5-dioxo-4,5-dihydro-3H-[1,2,4]triazin-2-yl]-benzamide;

3-(2-{4-Chloro-3-[(1-hydroxy-cycloheptylmethyl)-carbamoyl]-phenyl}-3,5-dioxo-2,5-dihydro-3H-[1,2,4]triazin-4-yl)-2-hydroxy-2-methyl-propionic acid methyl ester;

2-Chloro-N-(1-hydroxy-cycloheptylmethyl)-5-[4-(2-hydroxy-3-morpholin-4-yl-propyl)-3,5-dioxo-4,5-dihydro-3H-[1,2,4]triazin-2-yl]-benzamide;

5-[4-(3-Benzyloxy-2-hydroxy-propyl)-3,5-dioxo-4,5-dihydro-3H-[1,2,4]triazin-2-yl]-2-chloro-N-(1-hydroxy-cycloheptylmethyl)-benzamide;

2-Chloro-N-[2-(2-chloro-phenyl)-ethyl]-5-[4-(2-hydroxy-2-methyl-propyl)-3,5-dioxo-4,5-dihydro-3H-[1,2,4]triazin-2-yl]-benzamide;

2-Chloro-N-[2-(2-chloro-phenyl)-ethyl]-5-[4-(2-hydroxy-2-phenyl-ethyl)-3,5-dioxo-4,5-dihydro-3H-[1,2,4]triazin-2-yl]-benzamide;

2-Chloro-N-(2-hydroxy-cycloheptylmethyl)-5-[4-(2-hydroxy-2-methyl-propyl)-3,5-dioxo-4,5-dihydro-3H-[1,2,4]triazin-2-yl]-benzamide;

2-Chloro-N-(2-hydroxy-cycloheptylmethyl)-5-[4-(2-hydroxy-2-phenyl-ethyl)-3,5-dioxo-4,5-dihydro-3H-[1,2,4]triazin-2-yl]-benzamide;

2-Chloro-N-(2-hydroxy-cycloheptylmethyl)-5-[4-(2-hydroxy-3-methoxy-propyl)-3,5-dioxo-4,5-dihydro-3H-[1,2,4]triazin-2-yl)]-benzamide;

2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide;

2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide;

2-Chloro-5-[4-(2-hydroxy-2-methyl-propyl)-3,5-dioxo-4,5-dihydro-3H-[1,2,4]triazin-2-yl]-N-(2-hydroxy-2-phenyl-ethyl)-benzamide;

2-Chloro-5-[4-(2-hydroxy-3-methoxy-propyl)-3,5-dioxo-4,5-dihydro-3H-[1,2,4]triazin-2-yl]-N-phenethyl-benzamide; and 2-Chloro-5-[4-(2-hydroxy-2-methyl-propyl)-3,5-dioxo-4,5-dihydro-3H-[1,2,4]triazin-2-yl]-N-(2-hydroxy-2-phenyl-ethyl)-benzamide.

The present invention also provides the following preferred compounds of the present invention:

2-Chloro-N-(1-hydroxy-cyclohexylmethyl)-5-[4-(2-hydroxy-3-methoxy-propyl)-3,5-dioxo-4,5-dihydro-3H-[1,2,4]triazin-2-yl]-benzamide;

21-Chloro-5-[4-(2,3-dihydroxy-propyl)-3,5-dioxo-4,5-dihydro-3H-[1,2,4]triazin-2-yl]-N-(1-hydroxy-cyclohexylmethyl)-benzamide;

2-Chloro-N-(1-hydroxy-cycloheptylmethyl)-5-[4-(2-hydroxy-ethyl)-3,5-dioxo-4,5-dihydro-3H-[1,2,4]triazin-2-yl]-benzamide;

2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide;

2-Chloro-5-(4-cyanomethyl-3,5-dioxo-4,5-dihydro-3H-[1,2,4]triazin-2-yl)-N-(1-hydroxy-cycloheptylmethyl)-benzamide;

2-Chloro-5-[4-(2-hydroxy-3-methoxy-propyl)-3,5-dioxo-4,5-dihydro-3H-[1,2,4]triazin-2-yl]-N-(1-hydroxymethyl-cycloheptylmethyl)-benzamide;

2-Chloro-5-[4-(2-cyano-ethyl)-3,5-dioxo-4,5-dihydro-3H-[1,2,4]triazin-2-yl]-N-(1-hydroxy-cycloheptylmethyl)-benzamide;

N-(1-Hydroxy-cycloheptylmethyl)-5-[4-(2-hydroxy-ethyl)-3,5-dioxo-4,5-dihydro-3H-[1,2,4]triazin-2-yl]-2-methyl-benzamide;

2-Chloro-5-[4-(2,3-dihydroxy-propyl)-3,5-dioxo-4,5-dihydro-3H-[1,2,4]triazin-2-yl]-N-(1-hydroxy-cyclohexylmethyl)-benzamide;

2-Chloro-N-(1-hydroxy-cycloheptylmethyl)-5-[4-(2-hydroxy-2-methyl-propyl)-3,5-dioxo-4,5-dihydro-3H-[1,2,4]triazin-2-yl]-benzamide;

2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide;

2-Chloro-N-(1-hydroxy-cycloheptylmethyl)-5-[4-(2-hydroxy-2-phenyl-ethyl)-3,5-dioxo-4,5-dihydro-3H-[1,2,4]triazin-2-yl]-benzamide;

2-Chloro-5-[3,5-dioxo-4-(3,3,3-trifluoro-2-hydroxy-propyl)-4,5-dihydro-3H-[1,2,4]triazin-2-yl]-N-(1-hydroxy-cycloheptylmethyl)-benzamide;

2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide;

5-(4-Carbamoylmethyl-3,5-dioxo-4,5-dihydro-3H-[1,2,4]triazin-2-yl)-2-chloro-N-(1-hydroxy-cycloheptylmethyl)-benzamide;

2-Chloro-N-(1-hydroxy-cycloheptylmethyl)-5-[4-(2-methoxy-ethyl)-3,5-dioxo-4,5-dihydro-3H-[1,2,4]triazin-2-yl]-benzamide;

5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide;

5-[4-(3-Amino-2-hydroxy-propyl)-3,5-dioxo-4,5-dihydro-3H-[1,2,4]triazin-2-yl]-2-chloro-N-(1-hydroxy-cycloheptylmethyl)-benzamide; and 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide.

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^3$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays, Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

The present invention relates to a method for treating a IL-1 mediated disease in a mammal in need thereof, which comprises administering to said mammal an effective amount of a compound of formula I.

The present invention also relates to a method for treating an IL-1 mediated condition. As defined herein, a "IL-1 mediated condition" includes but is not limited to a disease or disorder selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, or muscle degeneration, in a mammal, including a human, comprising administering to said mammal an amount of a compound to formula I, effective in treating such a condition.

The present invention relates to a pharmaceutical composition for the treatment of a IL-1 mediated disease in a mammal which comprises an effective amount of a compound according to formula I and a pharmaceutically acceptable carrier.

The present invention relates to a pharmaceutical composition for the treatment of a IL-1 mediated condition in a mammal, including a human, comprising an amount of a compound to formula I, effective in treating such a condition and a pharmaceutically acceptable carrier.

Preferably, the compounds of the invention are useful for the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukemia, diabetes, Alzheimer's disease, meningitis, osteoporosis, burn injury, ischemic heart disease, stroke and varicose veins.

The present invention also provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

The invention further provides a method of treating osteoarthritis which comprises administering a therapeutically effective amount of a compound of formula (I), or a pharmaceutically acceptable salt or solvate thereof, as hereinbefore defined to a patient.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (I), or a pharmaceutically acceptable salt or solvate thereof, as hereinbefore defined to a patient.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

The present invention also relates to processes of preparing the compounds of formula I and intermediates used in such processes.

One embodiment of the processes of the invention relates to the preparation of compounds of formula I, which may be carried out by one or more of the synthetic methods outlined in Schemes I-IV, detailed below. The present invention also provides methods and intermediates useful in the synthesis of compounds of formula (I), and identified in Schemes I-IV below.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), COX-2 inhibitors (such as meloxicam, celecoxib, rofecoxib, valdecoxib, paracoxib, and etoricoxib) low dose methotrexate, lefunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist selected from the group consisting of zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonists for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including Inhibitors of the isoform PDE4D.

The present invention still further relates to the combination of a compound of the invention together with a antihistaminic $H_1$ receptor antagonists including cetirizine, loratadine, desloratadine, fexofenadine, astemizole, azelastine, and chlorpheniramine.

The present invention still further relates to the combination of a compound of the invention together with a gastroprotective $H_2$ receptor antagonist.

The present invention still further relates to the combination of a compound of the invention together with an $\alpha_1$- and $\alpha_2$-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents including ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, including prednisone, prednisolone, flunisolide, triamcinolone acetonide, beclomethasone dipropionate, budesonide, fluticasone propionate, and mometasone furoate.

The present invention still further relates to the combination of a compound of the invention together with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; (j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists selected from the group consisting of NKP-608C; SB-233412 (talnetant); and D-4418; and (t) elastase inhibitors selected from the group consisting of UT-77 and ZD-0892.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and farnesyl transferase inhibitors, VegF inhibitors, COX-2 inhibitors and antimetabolites such as methotrexate antineoplastic agents, especially antimitotic drugs including the vinca alkaloids such as vinblastine and vincristine.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

DETAILED DESCRIPTION OF THE INVENTION

Compounds of the formula I may be prepared according to the following reaction schemes and discussion. Unless otherwise indicated $R^1$ through $R^7$ in the reaction schemes and discussion that follows are as defined above.

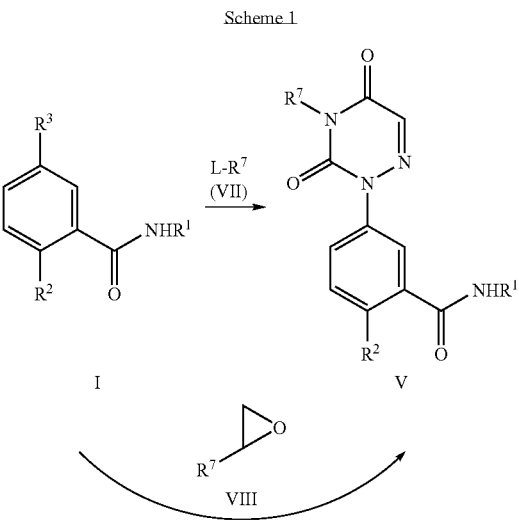

Scheme 1

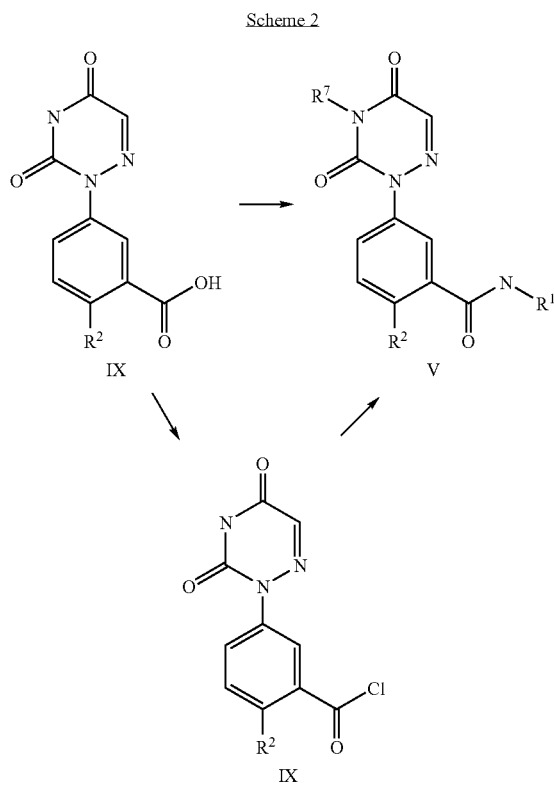

Scheme 2

Scheme 3

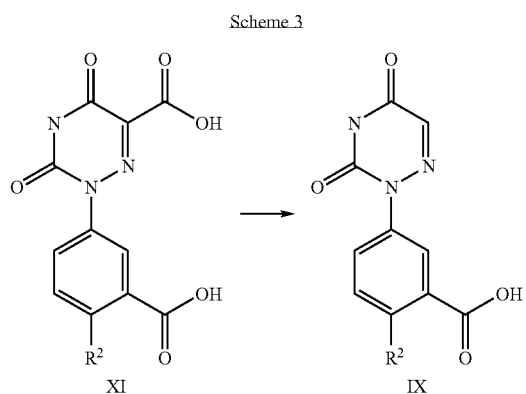

Scheme 4

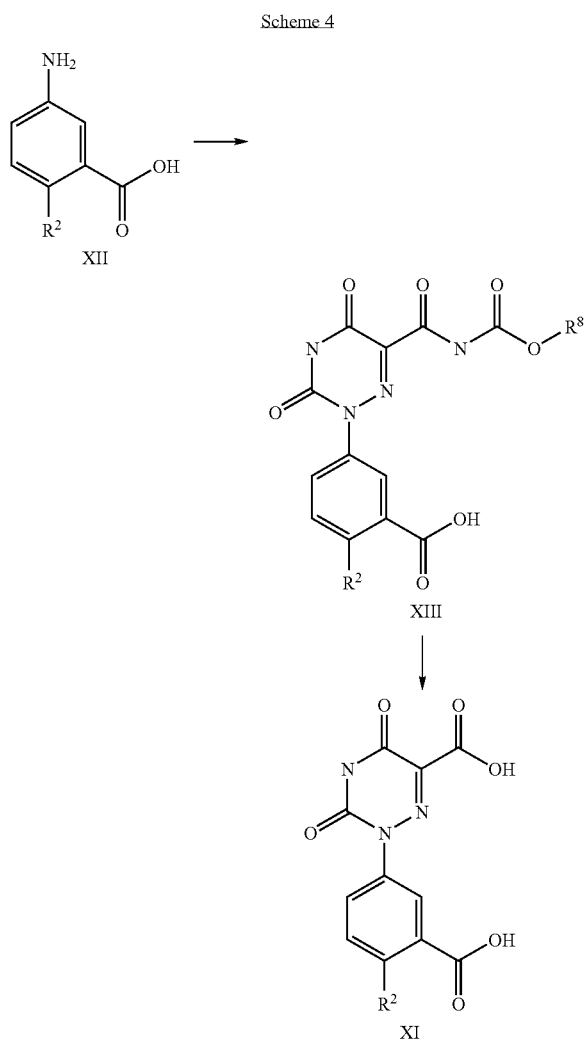

Scheme 1 refers to the preparation of compounds of the formula V. Compounds of the formula VI can be prepared from compounds of formula I by reaction with a compound of the formula VII in the presence of base, wherein L is a suitable leaving group, such as chloro, bromo, iodo tosylate or mesylate. Suitable bases include, but are not limited to, triethylamine, polymer supported BEMP, cesium carbonate, potassium carbonate, and sodium hydride, where cesium carbonate is preferred. The aforesaid reaction can be performed at temperatures ranging from 0° C. to 100° C. in the presence of a polar solvent including but not limited to dimethylsulfoxide, dimethylformamide, equal amounts of dimethylsulfoxide and acetone, or equal amounts of dimethylformamide and acetone, generally for a period of 2 hours to 72 hours, where the preferred conditions are dimethylsulfoxide at ambient temperature for 18 hours.

Compounds of the formula V may also be prepared from compounds of the formula I by reaction of an appropriately substituted epoxide of the formula VIII either neat or in the presence of a polar solvent including but not limited to dimethylformamide, dimethylsulfoxide, and tetrahydrofuran. The aforesaid reaction can be performed at temperatures ranging from 0° C. to 100° C. for a period of 2 to 72 hours, where the preferred conditions are dimethylforamide at 60° C. for 24 hours.

Scheme 2 refers to the preparation of compounds of the formula V. Compounds of the formula V can be prepared from compounds of formula IX by reacting with a compound of formula XIV, $H_2N-R^1$, in the presence of a coupling reagent such as 1-[3-(dimethylamino)propyl]-3-ethylcarbodiimide (EDCI), dicyclohexylcarbodiimide (DCC), 1,1'-carbonyldiimidazole (CDI) and a base such as dimethylaminopyridine (DMAP) or triethylamine in an aprotic solvent, such as methylene chloride, dimethylformamide, or dimethylsulfoxide, preferably 1-[3-(dimethylamino)propyl]-3-ethylcarbodiimide and dimethylaminopyridine in dimethyl formamide. The aforesaid reaction may be run at a temperature from 22° C. to 60° C., for a period of 1 hour to 20 hours, preferably 22° C. for 18 hours.

Compounds of the formula V may also be prepared from compounds of the formula X by reaction by reacting with a compound of formula XIV in the presence of a base including but not limited to dimethylaminopyridine (DMAP), triethylamine, aqueous sodium hydroxide or aqueous potassium hydroxide in an aprotic solvent, such as methylene chloride, ethyl acetate, dichloroethane, dimethylformamide, or dimethylsulfoxide, preferably aqueous sodium hydroxide and dichloroethane. The aforesaid reaction may be run at a temperature from 22° C. to 60° C., for a period of 1 hour to 24 hours, preferably at ambient temperature for 3 hours. Compound X can be prepared from compound IX by reaction with a reagent capable of generating an acid chloride such as thionyl chloride or oxalyl chloride in the presence of a polar aprotic solvent such as ethyl acetate, methylene chloride, or dichloroethane at a temperature of 22° C. to 60° C., for a period of 1 hour to 24 hours, preferably oxalyl chloride in methylene chloride at ambient temperature for 16 hours.

Scheme 3 refers to the preparation of compounds of the formula IX, which can be converted into compounds of formula V by the methods described in Scheme 2. Compounds of formula IX can be prepared from compounds of formula XI using decarboxylation conditions, preferably mercaptoacetic acid in water containing a base such as sodium hydroxide at a temperature from 22° C. to 160° C. for a period of 1 hour to 24 hours, preferably 100° C. for 18 hours.

Scheme 4 refers to the preparation of compounds of the formula XIII and XI, Compounds of the formula XI can be converted into compounds of the formula IX by the methods described in Scheme 3.

A compound of formula XI can be prepared from a compound of formula XIII, wherein $R^8$ is a suitable alkyl ($C_1$-$C_2$), by reaction with an acid such as 50% sulfuric acid at a temperature between 60° C. and 120° C., generally for a period between 30 minutes and 6 hours, preferably 2 hours at 120° C.

A compound of the formula XIII, wherein $R^8$ is a suitable alkyl ($C_1$-$C_2$), can be prepared from the diazonium intermediate derived from a compound of formula XIII. The diazonium intermediate is prepared by reaction of a compound of the formula XII with an acid such as hydrochloric acid and/or glacial acetic acid, followed by treatment with sodium nitrite in a solvent such as water at a temperature from 0° C. to 25° C., and the reaction is generally run from a period of 30 minutes to about 2 hours, preferably 10° C. for 30 minutes. A compound of the formula XII is prepared by the reaction of the above diazonium intermediate with a compound of the formula XVII: $R^8O(C=O)N(C=O)CH_2(C=O)N(C=O)OR^8$, under basic conditions. The reaction is typically carried out with sodium acetate as the base at a temperature from 0° C. to 120° C., preferably 10° C., then warmed to 120° C., and the reaction is generally run for a period of 1 hour to 24 hours, preferably 4 hours (Carrool, R. D.; et. al.; J. Med. Chem., 1983, 26, 96-100).

The activity of the compounds of the Invention for the various disorders described above can be determined according to one or more of the following assays. All of the compounds of the invention that were tested had an $IC_{50}$ of less than 10 μM in the in vitro assay described below.

Preferably, the compounds of the invention have an $IC_{50}$ in the in vitro assays described below of less than 100 nM, more preferably less than 50 nM, and most preferably less than 10 nM. Still further, the compounds of the invention preferably have an $IC_{50}$ in the range of 0.01 nM-100 nM, more preferably between 0.05 nM-50 nM, and most preferably between 0.10 nM-10 nM.

Pharmacological Analysis

Certain compounds such as benzoylbenzoyl adenosine triphosphate (bbATP) are known to be agonists of the $P2X_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. Alternatively, the propidium dye YOPRO-1 can be substituted for ethidium bromide so as to detect uptake of the dye. The increase in fluorescence can be used as a measure of $P2X_7$ receptor activation and therefore to quantify the effect of a compound on the $P2X_7$ receptor.

In this manner, the compounds of the invention can be tested for antagonist activity at the $P2X_7$ receptor. 96-Well flat bottomed microtitre plates are filled with 250 μl of test solution comprising 200 μl of a suspension of THP-1 cells (2.5×$10^6$ cells/ml, more preferably prestimulated as described in the literature with a combination of LPS and TNF to promote receptor expression) containing $10^{-4}$M ethidium bromide, 25 μl of a high potassium, low sodium buffer solution (10 mM Hepes, 150 mM KCl, 5 mM D-glucose and 1.0% FBS at pH 7.5) containing $10^{-5}$M bbATP, and 25/1 of the high potassium buffer solution containing 3×$10^{-5}$M test compound (more preferably 5×$10^{-4}$M, more preferably 1×$10^{-4}$M more preferably 1×$10^{-3}$M). The plate is covered with a plastic sheet and incubated at 37° C. for one hour. The plate is then read in a Perkin-Elmer fluorescent plate reader, excitation 520 nm, emission 595 nm, slit widths: Ex 15 nm, Em 20 nm. For the purposes of comparison, bbATP (a $P2X_7$ receptor agonist) and pyridoxal 5-phosphate (a $P2X_7$ receptor antagonist) can be used separately in the test as controls. From the readings obtained, a $pIC_{50}$ figure can be calculated for each test compound, this figure being the negative logarithm of the concentration of test compound necessary to reduce the bbATP agonist activity by 50%.

In like manner, the compounds of the invention can be tested for antagonist activity at the $P2X_7$ receptor using the cytokine IL-1β as the readout. Blood collected from normal volunteers in the presence of heparin is fractionated using lymphocyte separation medium obtained from Organon Technica (Westchester, Pa.). The region of the resulting gradient containing banded mononuclear cells is harvested, diluted with 10 ml of Maintenance Medium (RPMI 1640, 5% FBS, 25 mM Hepes, pH 7.2, 1% penicillin/streptomycin), and cells are collected by centrifugation. The resulting cell pellet was suspended in 10 ml of Maintenance Medium and a cell count was performed. In an average experiment, 2×$10^5$ mononuclear cells are seeded into each well of 96-well plates in a total volume of 0.1 ml. Monocytes are allowed to adhere for 2 hours, after which the supernatants are discarded and the attached cells are rinsed twice and then incubated in Maintenance Medium overnight at 37° C. in a 5% $CO_2$ environment.

The cultured monocytes can be activated with 10 ng/ml LPS (E. coli serotype 055:B5; Sigma Chemicals, St. Louis, Mo.). Following a 2-hour incubation, the activation medium is removed, the cells are rinsed twice with 0.1 ml of Chase Medium (RPMI 1640, 1% FBS, 20 mM Hepes, 5 mM $NaHCO_3$, pH 6.9), and then 0.1 ml of Chase Medium containing a test agent is added and the plate is incubated for 30 minutes; each test agent concentration can be evaluated in triplicate wells. ATP then is introduced (from a 100 mM stock solution, pH 7) to achieve a final concentration of 2 mM and the plate is incubated at 37° C. for an additional 3 hours. Media were harvested and clarified by centrifugation, and their IL-1β content was determined by ELISA (R&D Systems; Minneapolis, Minn.).

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), topical or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an Inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (inflammation) is 0.1 to 200 mg of the active ingredient per unit dose which could be administered, for example, 1 to 4 times per day.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Aerosol formulations for treatment of the conditions referred to above in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

Aerosol combination formulations for treatment of the conditions referred to above (e.g., adult respiratory distress syndrome) in the average adult human are preferably arranged so that each metered dose or "puff" of aerosol contains from about 1 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

Aerosol formulations for treatment of the conditions referred to above (e.g., adult respiratory distress syndrome) in the average adult human are preferably arranged so that each metered dose or "puff" of aerosol contains from about 20 µg to 1000 µg of the compound of the invention. The overall daily dose with an aerosol will be within the range 100 µg to 10 mg of the $P2X_7$ receptor inhibitor. Administration may be several times daily, for example 2, 3, 4 or 8 times, giving for example, 1, 2 or 3 doses each time.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatography. The following solvents and gradients were used for the analysis. Solvent A; 98% water/2% acetonitrile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 AMU to 1100 AMU. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32-63 mm silica gel and executed under nitrogen pressure (flash chromatography) conditions. Room or ambient temperature refers to 20-25° C. All non-aqueous reactions were run under a nitrogen atmosphere for convenience and to maximize yields. Concentration at reduced pressure means that a rotary evaporator was used.

One of ordinary skill in the art will appreciate that in some cases protecting groups may be required during preparation. After the target molecule is made, the protecting group can be removed by methods well known to those of ordinary skill in the art, such as described in Greene and Wuts, "Protective Groups in Organic Synthesis" (3rd Ed, John Wiley & Sons 1999).

EXAMPLE 1

5-(4-Carbamoylmethyl-3,5-dioxo-4,5-dihydro-3H-[1,2,4]triazin-2-yl)-N-(1-hydroxy-cycloheptylmethyl)-2-methyl-benzamide

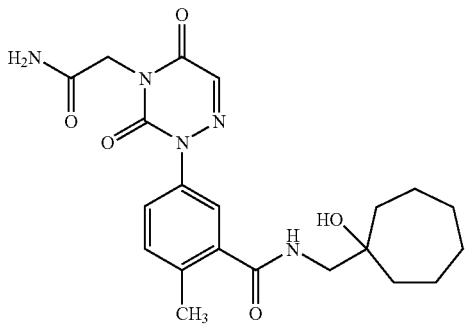

(A) 5-Amino-2-methyl-benzoic acid hydrochloride salt

A slurry of 5-nitro-2-methyl-benzoic acid (17.1 g, 94.4 mmol) and 10% Pd/C (500 mg) in EtOH (500 mL) was shaken under 40 psi $H_2$ at ambient temperature for 4 hours. HCl was added and the solution filtered through a pad of celite. The filtrate was concentrated in vacuo to give the title compound (17.2 g).

(B) 2-(3-Carboxy-4-methyl-phenyl)-3,5-dioxo-2,3,4,5-tetrahydro-[1,2,4]triazine-6-carboxylic acid To a solution of 5-Amino-2-methyl-benzoic acid hydrochloride salt (15.2 g, 81.2 mmol) in acetic acid (300 mL) was added concentrated HCl (21.0 mL). The resulting slurry was stirred at ambient temperature for 30 minutes. The reaction was then cooled to 10° C., and a solution of sodium nitrite (6.17 g, 89.4 mmol) in water (15 mL) was added dropwise. The reaction was stirred at 10° C. for 30 minutes, when sodium acetate (14.7 g, 179.0 mmol) and (3-ethoxycarbonylamino-3-oxo-propionyl)-carbamic acid ethyl ester (*J. Chem. Soc. Perkins Trans*. I, 1991, 2317) (22.0 g, 89.4 mmol) were added. The reaction was let stir at 10° C. for 20 minutes, then warmed to room temperature and stirred for 1 hour. Sodium acetate (6.7 g, 81.2 mmol) was then added and the reaction refluxed for 14 hours. A 50% aqueous solution of $H_2SO_4$ (88.0 mL) was added and the reaction refluxed for 2 hours. The reaction was cooled, then water (50 mL) added. The resulting tan precipitate was filtered, washed with water, and dried to give the title compound (17.8 g).

(C) 5-(3,5-Dioxo-4,5-dihydro-3H-[1,2,4]triazin-2-yl)-2-methyl-benzoic acid 2-(3-Carboxy-4-methyl-phenyl)-3,5-dioxo-2,3,4,5-tetrahydro-[1,2,4]triazine-6-carboxylic acid (110 gm) was added to 8 volumes of water with 2.4 equivalents of sodium hydroxide and 1.1 equivalents of mercaptoacetic acid. The reaction mixture was heated to reflux (100-105° C.) for approximately 18 hours at which point the reaction was complete by HPLC. 30% Sodium hydroxide and toluene were added and the resulting mixture was stirred. Upon settling a large interface was noted. More water, toluene and some ethyl acetate were added. The interface was minimized. The water layer was separated and treated with 2N HCl. At pH 2 solids precipitated out and the slurry was cooled to <10° C. The solids were filtered off in a slow filtration and dried in a vacuum oven to give 69 gm of the title compound.

(D) 5-(3,5-Dioxo-4,5-dihydro-3H-[1,2,4]triazin-2-yl)-N-(1-hydroxy-cycloheptylmethyl)-2-methyl-benzamide A slurry of 5-(3,5-Dioxo-4,5-dihydro-3H-[1,2,4]triazin-2-yl)-2-methyl-benzoic acid (5.0 g, 20.2 mmol), 1-aminomethyl-cycloheptanol HCl (5.4 g, 30.3 mmol), EDCI (5.8 g), and DMAP (7.4 g, 60.6 mmol) in DMF (67.3 mL) was stirred at ambient temperature for 14 hours. The reaction was then poured into 1N HCl (50 mL) and diluted with water (15 fold). The aqueous was extracted with $CH_2Cl_2$ (3×). The organics were combined, washed with brine, dried over sodium sulfate, and concentrated in vacuo to give a tan solid. The crude was recrystallized from $CH_2Cl_2$ to give the title compound as an off-white solid (3.1 g).

(E) 5-(4-Carbamoylmethyl-3,5-dioxo-4,5-dihydro-3H-[1,2,4]triazin-2-yl)-N-(1-hydroxy-cycloheptylmethyl)-2-methyl-benzamide A slurry of 5-(3,5-Dioxo-4,5-dihydro-3H-[1,2,4]triazin-2-yl)-N-(1-hydroxy-cycloheptylmethyl)-2-methyl-benzamide (200.0 mg, 0.537 mmol) and $Cs_2CO$, (290.3 mg, 0.891 mmol) were stirred in DMSO (1.79 mL, 0.3 M) at ambient temperature for 15 minutes. 2-Bromoacetamide (74.1 mg, 0.537 mmol) was added and the reaction stirred at ambient temperature for 14 hours. The reaction was diluted with water (15-fold) and the aqueous extracted with $CH_2Cl_2$ (3×). The organics were dried over sodium sulfate, and concentrated in vacuo to a tan oil. The crude was triturated from $IPE/Et_2O/CH_2Cl_2$ to give the title compound as a tan solid (105 mg). LCMS (m/z) 430.5 M+1.

The compounds of Examples 2-43, identified in Table 1 below, can be prepared according to the method of Example 1.

TABLE 1

| EXAMPLE | STRUCTURE | NAME | DATA LCMS M/Z |
|---|---|---|---|
| 2 | 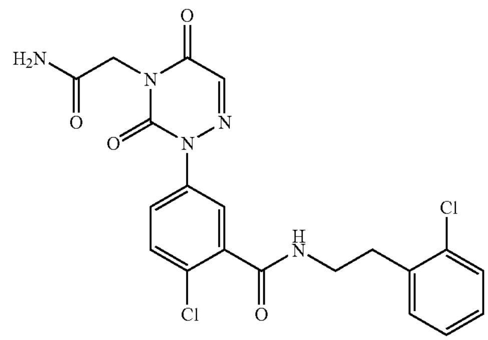 | 5-(4-Carbamoylmethyl-3,5-dioxo-4,5-dihydro-3H-[1,2,4]triazin-2-yl)-2-chloro-N-[2-(2-chloro-phenyl)-ethyl]-benzamide | 462.1 |
| 3 | 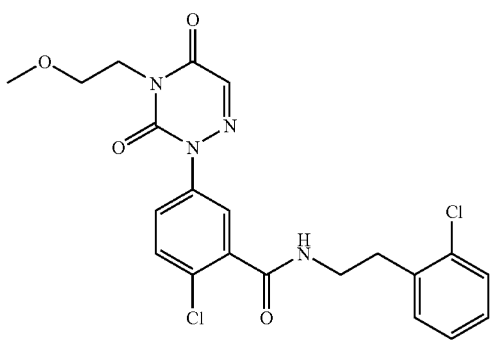 | 2-Chloro-N-[2-(2-chloro-phenyl)-ethyl]-5-[4-(2-methoxy-ethyl)-3,5-dioxo-4,5-dihydro-3H-[1,2,4]triazin-2-yl]-benzamide | 463.2 |
| 4 | 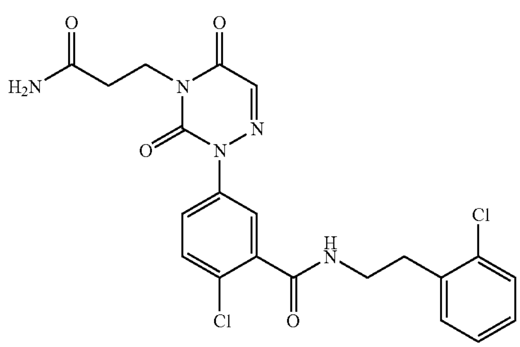 | 5-[4-(2-Carbamoyl-ethyl)-3,5-dioxo-4,5-dihydro-3H-[1,2,4]triazin-2-yl]-2-chloro-N-[2-(2-chloro-phenyl)-ethyl]-benzamide | 476.3 |
| 5 | 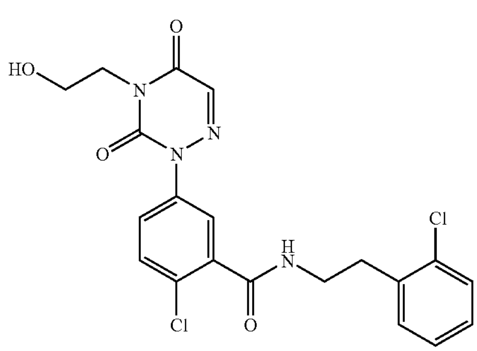 | 2-Chloro-N-[2-(2-chloro-phenyl)-ethyl]-5-[4-(2-hydroxy-ethyl)-3,5-dioxo-4,5-dihydro-3H-[1,2,4]triazin-2-yl]-benzamide | 449.4 |

TABLE 1-continued

| EXAMPLE | STRUCTURE | NAME | DATA LCMS M/Z |
|---|---|---|---|
| 6 | 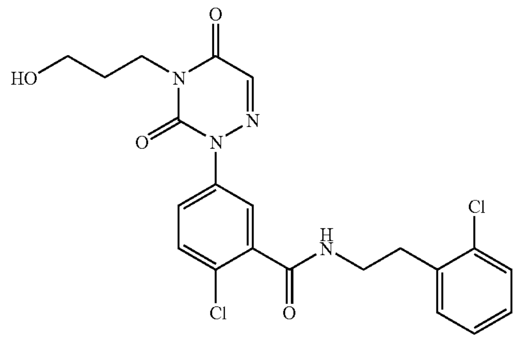 | 2-Chloro-N-[2-(2-chloro-phenyl)-ethyl]-5-[4-(3-hydroxy-propyl)-3,5-dioxo-4,5-dihydro-3H-[1,2,4]triazin-2-yl]-benzamide | 463.6 |
| 7 | 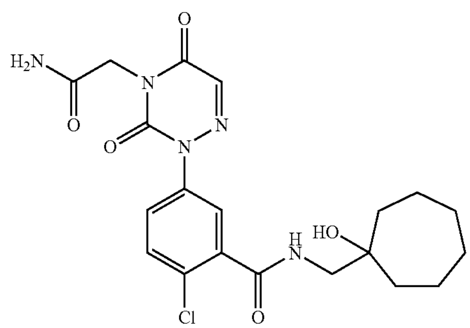 | 5-(4-Carbamoylmethyl-3,5-dioxo-4,5-dihydro-3H-[1,2,4]triazin-2-yl)-2-chloro-N-(1-hydroxy-cycloheptylmethyl)-benzamide | 450.9 |
| 8 | 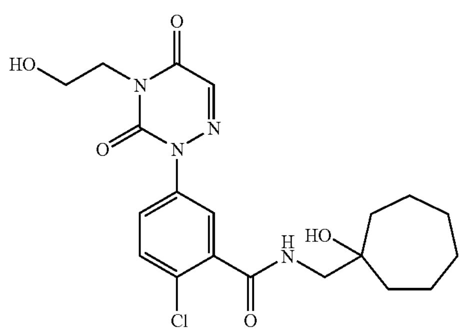 | 2-Chloro-N-(1-hydroxy-cycloheptylmethyl)-5-[4-(2-hydroxy-ethyl)-3,5-dioxo-4,5-dihydro-3H-[1,2,4]triazin-2-yl]-benzamide | 437.9 |
| 9 | 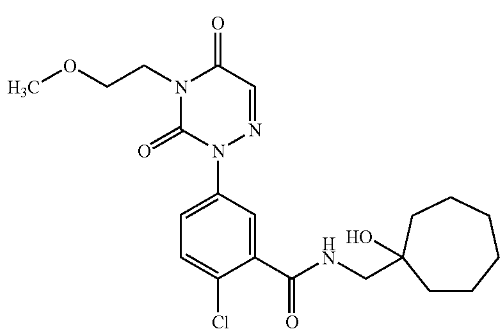 | 2-Chloro-N-(1-hydroxy-cycloheptylmethyl)-5-[4-(2-methoxy-ethyl)-3,5-dioxo-4,5-dihydro-3H-[1,2,4]triazin-2-yl]-benzamide | 451.7 |

TABLE 1-continued

| EXAMPLE | STRUCTURE | NAME | DATA LCMS M/Z |
|---|---|---|---|
| 10 | 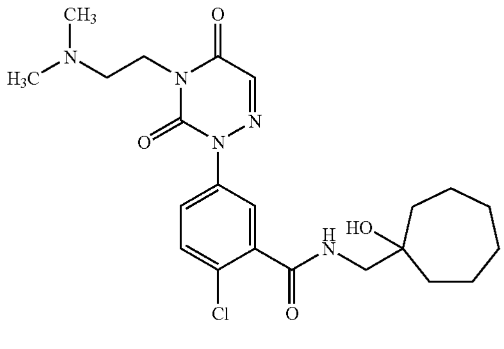 | 2-Chloro-5-[4-(2-dimethylamino-ethyl)-3,5-dioxo-4,5-dihydro-3H-[1,2,4]triazin-2-yl]-N-(1-hydroxy-cycloheptylmethyl)-benzamide | 464.5 |
| 11 | 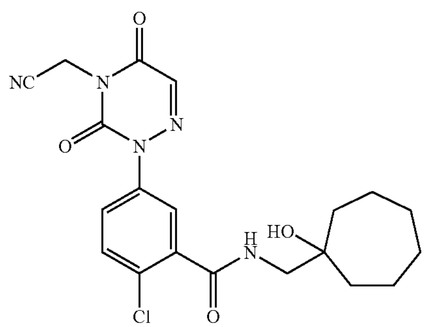 | 2-Chloro-5-(4-cyanomethyl-3,5-dioxo-4,5-dihydro-3H-[1,2,4]triazin-2-yl)-N-(1-hydroxy-cycloheptylmethyl)-benzamide | 432.3 |
| 12 | 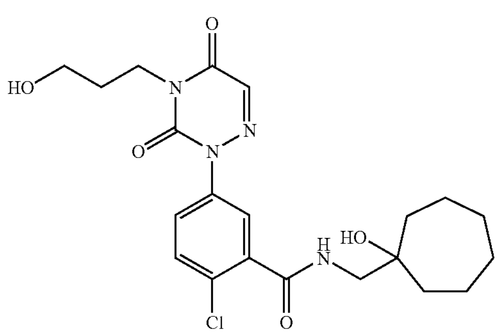 | 2-Chloro-N-(1-hydroxy-cycloheptylmethyl)-5-[4-(3-hydroxy-propyl)-3,5-dioxo-4,5-dihydro-3H-[1,2,4]triazin-2-yl]-benzamide | 451.4 |
| 13 | 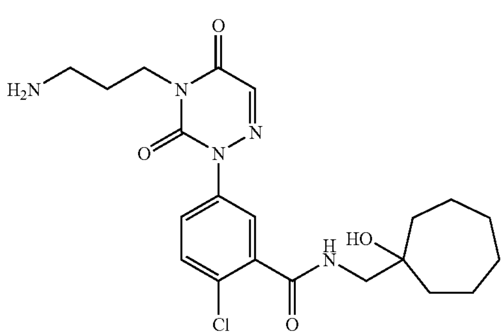 | 5-[4-(2-Amino-ethyl)-3,5-dioxo-4,5-dihydro-3H-[1,2,4]triazin-2-yl]-2-chloro-N-(1-hydroxy-cycloheptylmethyl)-benzamide | 436.5 |

TABLE 1-continued

| EXAMPLE | STRUCTURE | NAME | DATA LCMS M/Z |
|---|---|---|---|
| 14 | 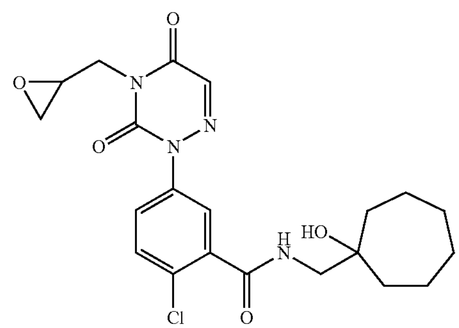 | 2-Chloro-N-(1-hydroxy-cycloheptylmethyl)-5-(4-oxiranylmethyl-3,5-dioxo-4,5-dihydro-3H-[1,2,4]triazin-2-yl)-benzamide | 449.5 |
| 15 | 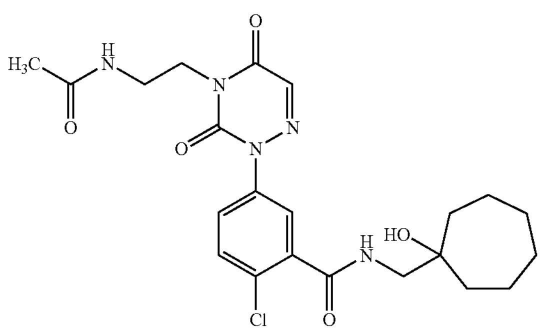 | 5-[4-(2-Acetylamino-ethyl)-3,5-dioxo-4∽5-dihydro-3H-[1,2,4]triazin-2-yl]-2-chloro-N-(1-hydroxy-cycloheptylmethyl)-benzamide | 478.4 |
| 16 | 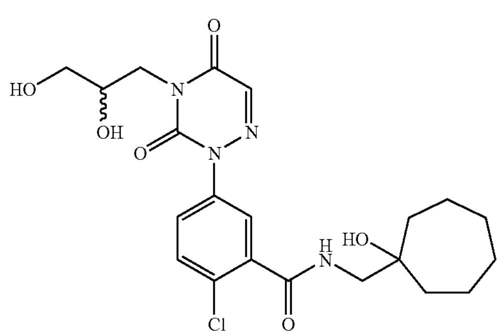 | 2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide | 467.4 |
| 17 | 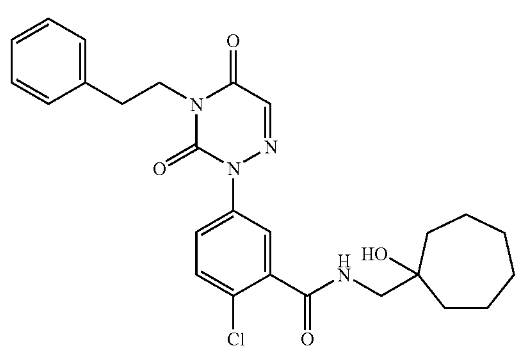 | 2-Chloro-5-(3,5-dioxo-4-phenethyl-4,5-dihydro-[1,2,4]triazin-2-yl)-N-(1-hydroxy-cycloheptylmethyl)-benzamide | 497.5 |

TABLE 1-continued

| EXAMPLE | STRUCTURE | NAME | DATA LCMS M/Z |
|---|---|---|---|
| 18 | 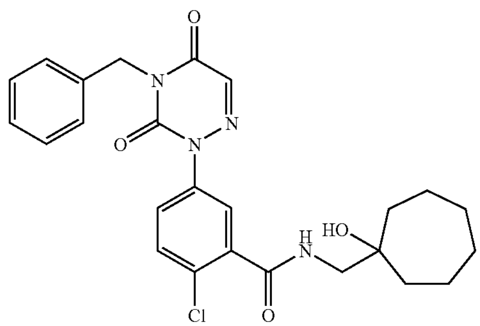 | 5-(4-Benzyl-3,5-dioxo-4,5-dihydro-3H-[1,2,4]triazin-2-yl)-2-chloro-N-(1-hydroxy-cycloheptylmethyl)-benzamide | 483.5 |
| 19 | 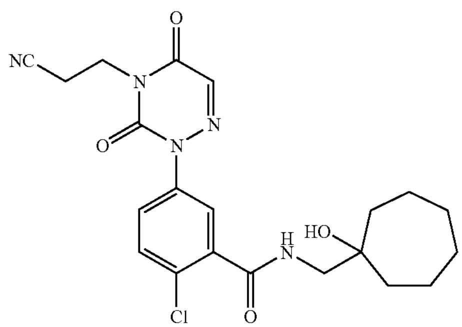 | 2-Chloro-5-[4-(2-cyano-ethyl)-3,5-dioxo-4,5-dihydro-3H-[1,2,4]triazin-2-yl]-N-(1-hydroxy-cycloheptylmethyl)-benzamide | 446.5 |
| 20 | 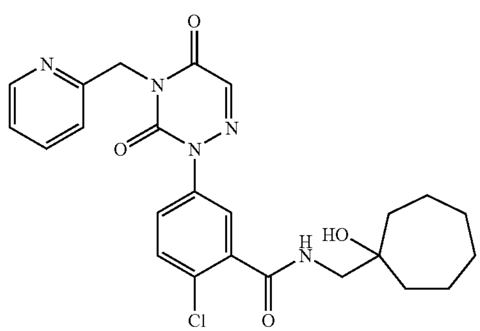 | 2-Chloro-5-(3,5-dioxo-4-pyridin-2-ylmethyl-4,5-dihydro-3H-[1,2,4]triazin-2-yl)-N-(1-hydroxy-cycloheptylmethyl)-benzamide | 484.4 |
| 21 | 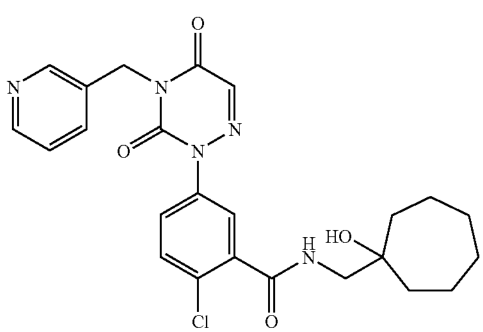 | 2-Chloro-5-(3,5-dioxo-4-pyridin-3-ylmethyl-4,5-dihydro-3H-[1,2,4]triazin-2-yl)-N-(1-hydroxy-cycloheptylmethyl)-benzamide | 484.5 |

TABLE 1-continued

| EXAMPLE | STRUCTURE | NAME | DATA LCMS M/Z |
|---|---|---|---|
| 22 | 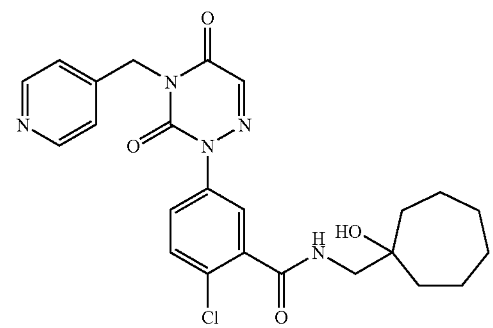 | 2-Chloro-5-(3,5-dioxo-4-pyridin-4-ylmethyl-4,5-dihydro-3H-[1,2,4]triazin-2-yl)-N-(1-hydroxy-cycloheptylmethyl)-benzamide | 484.5 |
| 23 | 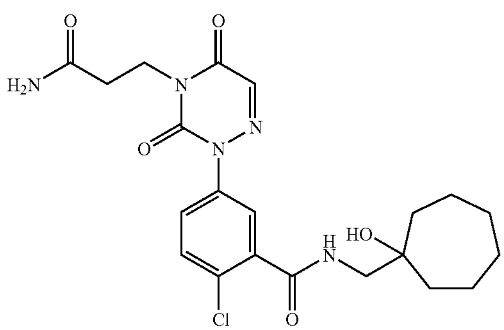 | 5-[4-(2-Carbamoyl-ethyl)-3,5-dioxo-4,5-dihydro-3H-[1,2,4]triazin-2-yl]-2-chloro-N-(1-hydroxy-cycloheptylmethyl)-benzamide | 474.5 |
| 24 | 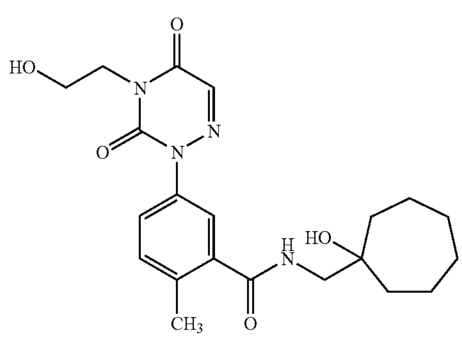 | N-(1-Hydroxy-cycloheptylmethyl)-5-[4-(2-hydroxy-ethyl)-3,5-dioxo-4,5-dihydro-3H-[1,2,4]triazin-2-yl]-2-methyl-benzamide | 417.5 |
| 25 | 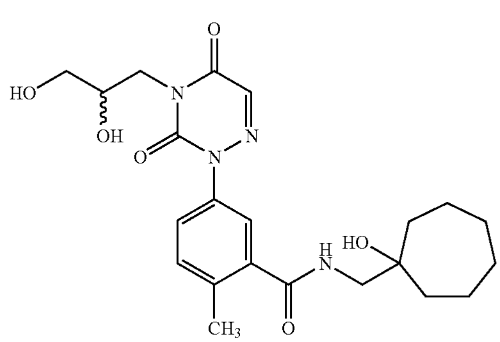 | 5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide | 447.3 |

TABLE 1-continued

| EXAMPLE | STRUCTURE | NAME | DATA LCMS M/Z |
|---|---|---|---|
| 26 | 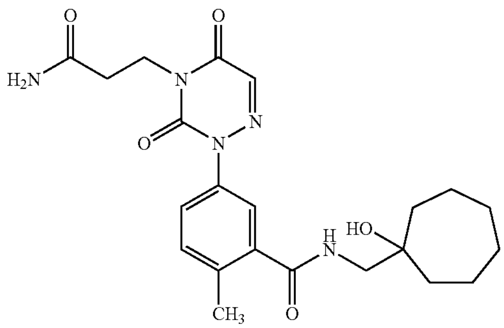 | 5-[4-(2-Carbamoyl-ethyl)-3,5-dioxo-4,5-dihydro-3H-[1,2,4]triazin-2-yl]-N-(1-hydroxy-cycloheptylmethyl)-2-methyl-benzamide | 444.6 |
| 27 | 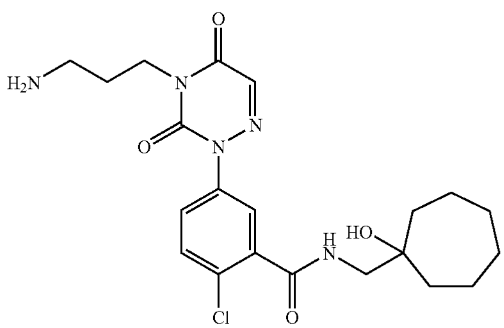 | 5-[4-(3-Amino-propyl)-3,5-dioxo-4,5-dihydro-3H-[1,2,4]triazin-2-yl]-2-chloro-N-(1-hydroxy-cycloheptylmethyl)-benzamide | 450.4 |
| 28 | 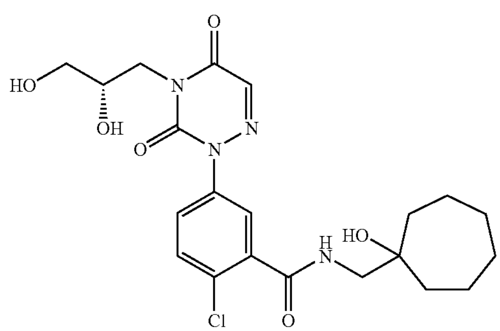 | 2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide | 467.4 |
| 29 | 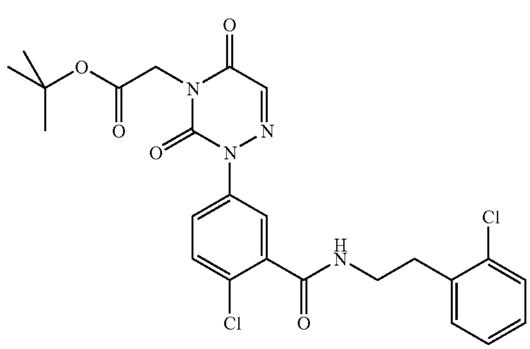 | (2-{4-Chloro-3-[2-(2-chloro-phenyl)-ethylcarbamoyl]-phenyl}-3,5-dioxo-2,5-dihydro-3H-[1,2,4]triazin-4-yl)-acetic acid tert-butyl ester | 519.7 |

TABLE 1-continued

| EXAMPLE | STRUCTURE | NAME | DATA LCMS M/Z |
|---|---|---|---|
| 30 | 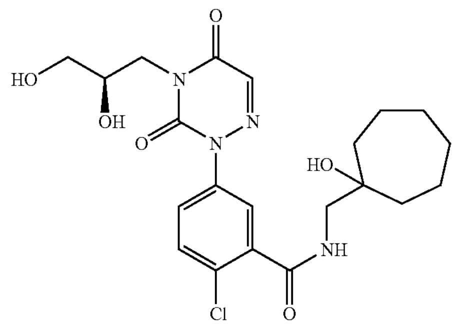 | 2-Chloro-5-[4-(2,3-dihydroxy-propyl)-3,5-dioxo-4,5-dihydro-3H-[1,2,4]triazin-2-yl]-N-(1-hydroxy-cycloheptylmethyl)-benzamide | 467.6 |
| 31 | 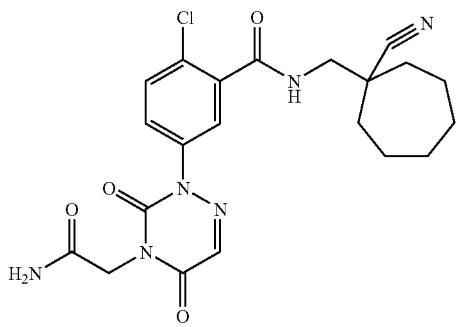 | 5-(4-Carbamoylmethyl-3,5-dioxo-4,5-dihydro-3H-[1,2,4]triazin-2-yl]-2-chloro-N-(1-cyano-cycloheptylmethyl)-benzamide | 459.3 |
| 32 | 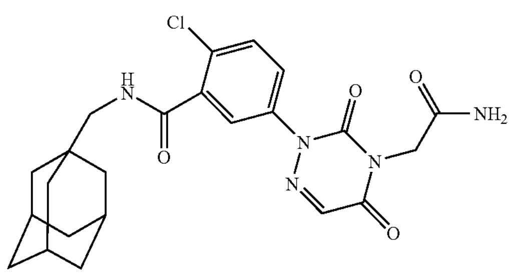 | N-Adamantan-1-ylmethyl-5-(4-carbamoylmethyl-3,5-dioxo-4,5-dihydro-3H-[1,2,4]triazin-2-yl)-2-chloro-benzamide | 473.0 |
| 33 | 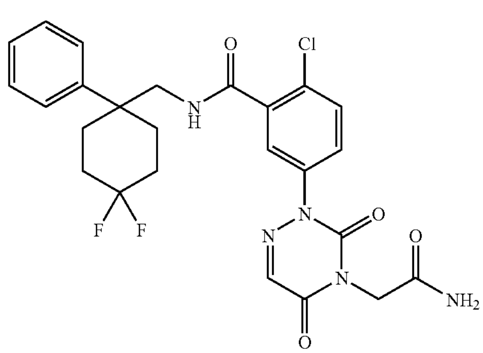 | 5-(4-Carbamoylmethyl-3,5-dioxo-4,5-dihydro-3H-[1,2,4]triazin-2-yl)-2-chloro-N-(4,4-difluoro-1-phenyl-cyclohexylmethyl)-benzamide | 532.3 |

TABLE 1-continued

| EXAMPLE | STRUCTURE | NAME | DATA LCMS M/Z |
|---|---|---|---|
| 34 | 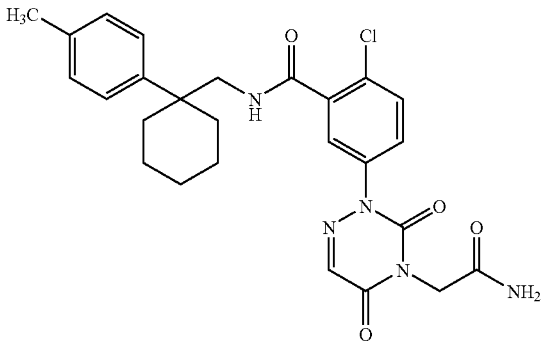 | 5-(4-Carbamoylmethyl-3,5-dioxo-4,5-dihydro-3H-[1,2,4]triazin-2-yl)-2-chloro-N-(1-p-tolyl-cyclohexylmethyl)-benzamide | 510.4 |
| 35 | 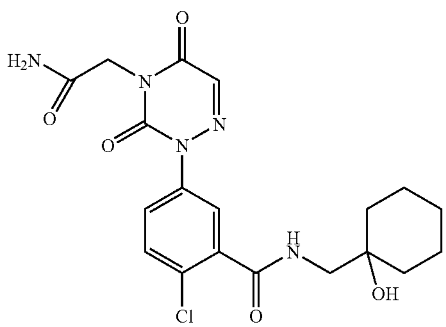 | 5-(4-Carbamoylmethyl-3,5-dioxo-4,5-dihydro-3H-[1,2,4]triazin-2-yl)-2-chloro-N-(1-hydroxy-cyclohexylmethyl)-benzamide | 436.5 |
| 36 | 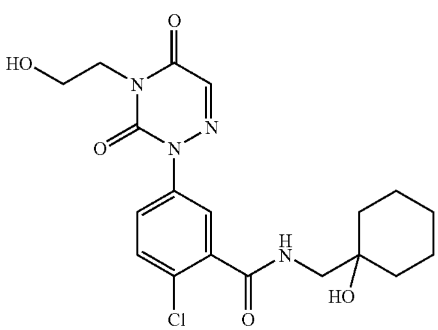 | 2-Chloro-N-(1-hydroxy-cyclohexylmethyl)-5-[4-(2-hydroxy-ethyl)-3,5-dioxo-4,5-dihydro-3H-[1,2,4]triazin-2-yl]-benzamide | 423.5 |
| 37 | 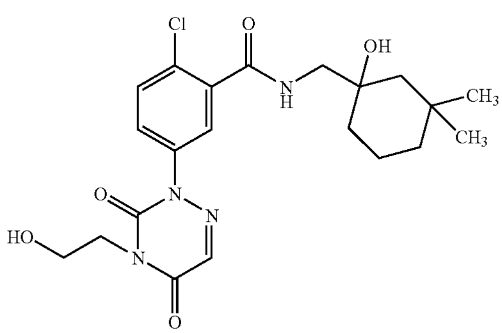 | 2-Chloro-N-(1-hydroxy-3,3-dimethyl-cyclohexylmethyl)-5-[4-(2-hydroxy-ethyl)-3,5-dioxo-4,5-dihydro-3H-[1,2,4]triazin-2-yl]-benzamide | 451.5 |

TABLE 1-continued

| EXAMPLE | STRUCTURE | NAME | DATA LCMS M/Z |
|---|---|---|---|
| 38 | 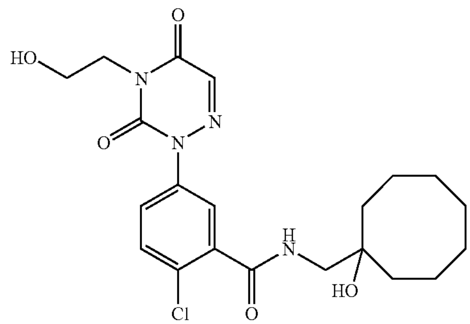 | 2-Chloro-N-(1-hydroxy-cyclooctylmethyl)-5-[4-(2-hydroxy-ethyl)-3,5-dioxo-4,5-dihydro-3H-[1,2,4]triazin-2-yl]-benzamide | 451.5 |
| 39 | 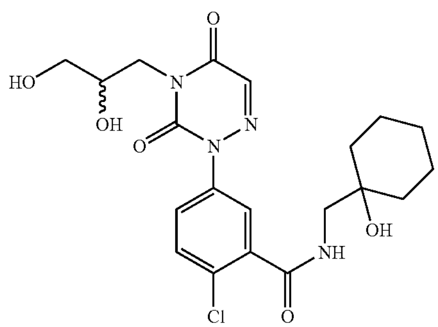 | 2-Chloro-5-[4-(2,3-dihydroxy-propyl)-3,5-dioxo-4,5-dihydro-3H-[1,2,4]triazin-2-yl]-N-(1-hydroxy-cyclohexylmethyl)-benzamide | 453.5 |
| 40 | 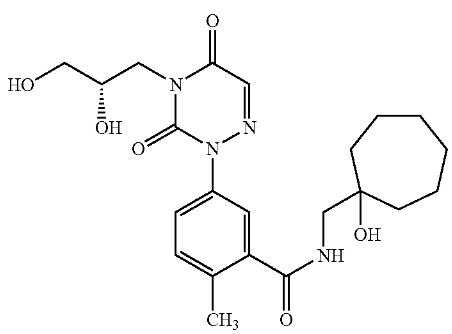 | 5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide | 447.6 |
| 41 | 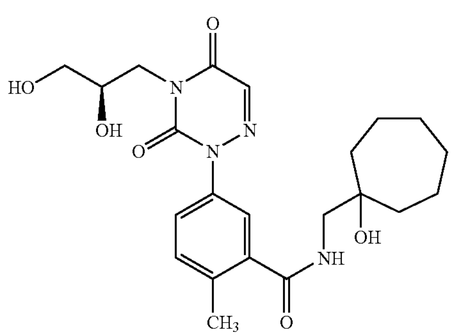 | 5-[4-(2,3-Dihydroxy-propyl)-3,5-dioxo-4,5-dihydro-3H-[1,2,4]triazin-2-yl]-N-(1-hydroxy-cycloheptylmethyl)-2-methyl-benzamide | 447.6 |

TABLE 1-continued

| EXAMPLE | STRUCTURE | NAME | DATA LCMS M/Z |
|---|---|---|---|
| 42 | 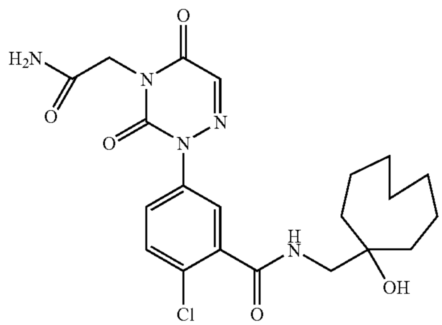 | 5-(4-Carbamoylmethyl-3,5-dioxo-4,5-dihydro-3H-[1,2,4]triazin-2-yl)-2-chloro-N-(1-hydroxy-cyclooctylmethyl)-benzamide | 462.4 (M − 1) |
| 43 | 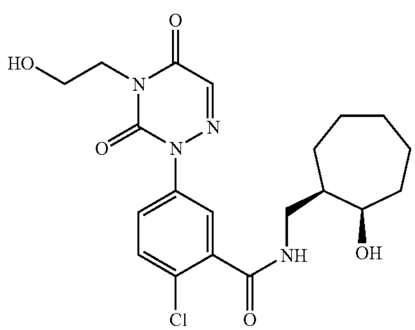 | 2-Chloro-N-(2-hydroxy-cycloheptylmethyl)-5-[4-(2-hydroxy-ethyl)-3,5-dioxo-4,5-dihydro-3H-[1,2,4]triazin-2-yl]-benzamide | 437.3 |
| 44 | 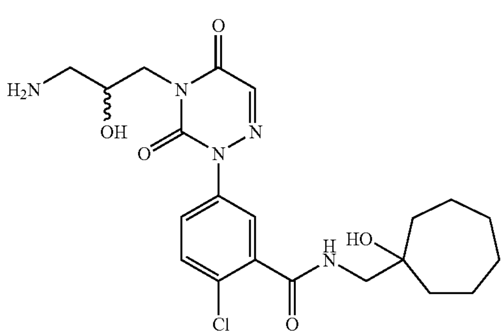 | 5-[4-(3-Amino-2-hydroxy-propyl)-3,5-dioxo-4,5-dihydro-3H-[1,2,4]triazin-2-yl]-2-chloro-N-(1-hydroxy-cycloheptylmethyl)-benzamide | 448.5 |

EXAMPLE 45

2-Chloro-N-[2-(2-chloro-phenyl)-ethyl]-5-(4-methylcarbamoylmethyl-3,5-dioxo-4,5-dihydro-3H-[1,2,4]triazin-2-yl)-benzamide

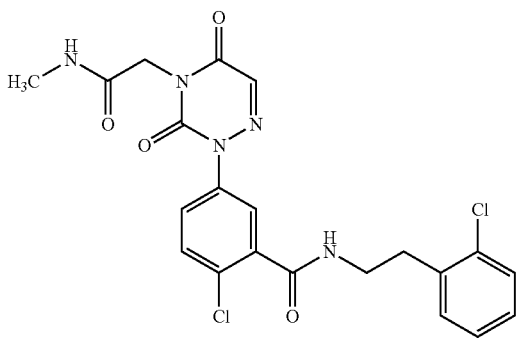

(A) (2-{4-Chloro-3-[2-(2-chloro-phenyl)-ethylcarbamoyl]-phenyl}-3,5-dioxo-2,5-dihydro-3H-[1,2,4]triazin-4-yl)-acetic acid A solution of Example 34 (358 mg, 0.69 mmol) and TFA (1 mL) was stirred at ambient temperature for 18 hours. The solvent was removed in vacuo, and excess TFA azeotroped using $CH_2Cl_2$ (3×). The crude pale brown solid was triturated in hexane to give the title compound (295 mg).

(B) 2-Chloro-N-[2-(2-chloro-phenyl)-ethyl]-5-(4-methylcarbamoylmethyl-3,5-dioxo-4,5-dihydro-3H-[1,2,4]triazin-2-yl)-benzamide A slurry of (2-{4-Chloro-3-[2-(2-chloro-phenyl)-ethylcarbamoyl]-phenyl}-3,5-dioxo-2,5-dihydro-3H-[1,2,4]triazin-4-yl)-acetic acid (71.4 mg, 0.154 mmol), methylamine HCl (15.6 mg, 0.231 mmol), EDCI (44.4 mg, 0.231 mmol), and DMAP (75.5 mg, 0.616 mmol) in DMF (1.0 mL) were stirred at ambient temperature for 20 hours. The reaction was diluted with 1N HCl, and let stir for 5 hours. The crude was filtered and triturated from hexane to give the title compound (20 mg). LCMS (m/z) 476.1 M+1.

The compounds of Examples 46-60, identified in Table 2 below, can be prepared according to the method of Example 45.

TABLE 2

| EXAMPLE | STRUCTURE | NAME | DATA LCMS M/Z |
|---|---|---|---|
| 46 | 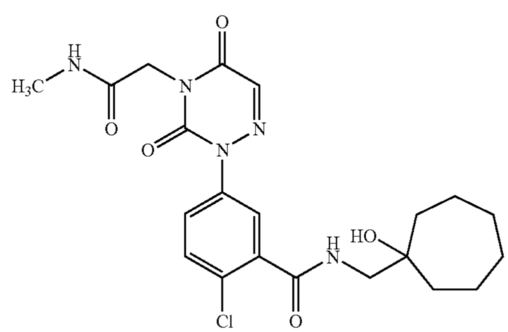 | 2-Chloro-N-(1-hydroxy-cycloheptylmethyl)-5-(4-methylcarbamoylmethyl-3-5-dioxo-4,5-dihydro-3H-[1,2,4]triazin-2-yl)-benzamide | 464.8 |
| 47 | 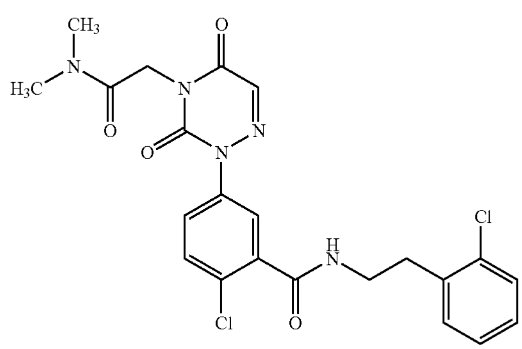 | 2-Chloro-N-[2-(2-chloro-phenyl)-ethyl]-5-(4-dimethylcarbamoylmethyl-3,5-dioxo-4,5-dihydro-3H-[1,2,4]triazin-2-yl)-benzamide | 490.1 |

TABLE 2-continued

| EXAMPLE | STRUCTURE | NAME | DATA LCMS M/Z |
|---|---|---|---|
| 48 | 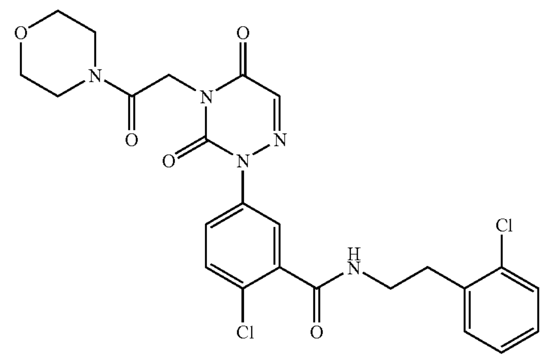 | 2-Chloro-N-[2-(2-chloro-phenyl)-ethyl]-5-[4-(2-morpholin-4-yl-2-oxo-ethyl)-3,5-dioxo-4,5-dihydro-3H-[1-2,4]triazin-2-yl]-benzamide | 523.3 |
| 49 | 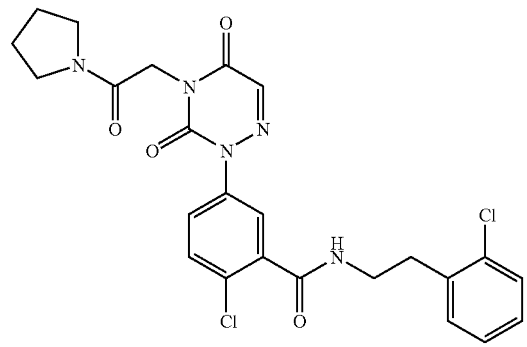 | 2-Chloro-N-[2-(2-chloro-phenyl)-ethyl]-5-[3,5-dioxo-4-(2-oxo-2-pyrrolidin-1-yl-ethyl)-4,5-dihydro-3H-[1,2,4]triazin-2-yl]-benzamide | 516.3 |
| 50 | 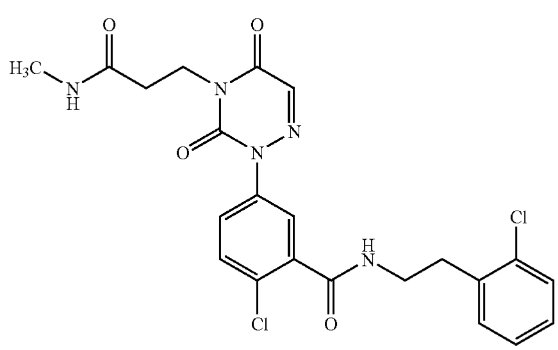 | 2-Chloro-N-[2-(2-chloro-phenyl)-ethyl]-5-[4-(2-methylcarbamoyl-ethyl)-3,5-dioxo-4,5-dihydro-3H-[1,2,4]triazin-2-yl]-benzamide | 490.9 |
| 51 | 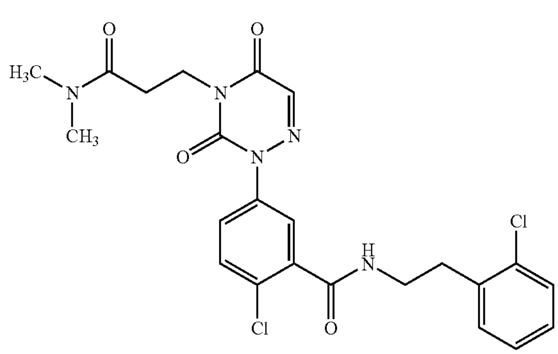 | 2-Chloro-N-[2-(2-chloro-phenyl)-ethyl]-5-[4-(2-dimethylcarbamoyl-ethyl)-3,5-dioxo-4,5-dihydro-3H-[1,2,4]triazin-2-yl]-benzamide | 504.5 |

TABLE 2-continued

| EXAMPLE | STRUCTURE | NAME | DATA LCMS M/Z |
|---|---|---|---|
| 52 | 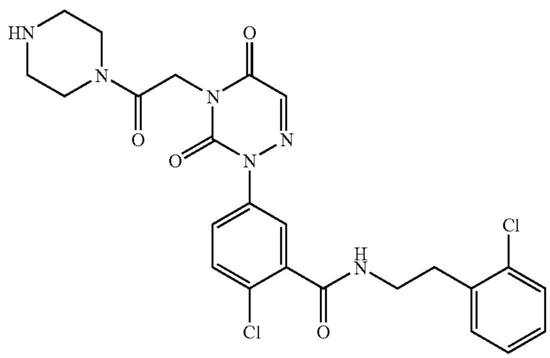 | 2-Chloro-N-[2-(2-chlorophenyl)-ethyl]-5-[3,5-dioxo-4-(2-oxo-2-piperazin-1-yl-ethyl)-4,5-dihydro-3H-[1,2,4]triazin-2-yl]-benzamide | 531.5 |
| 53 | 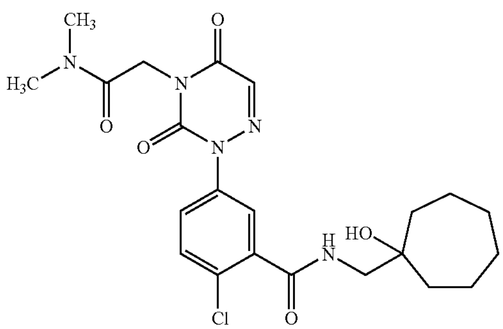 | 2-Chloro-5-(4-dimethylcarbamoylmethyl-3,5-dioxo-4,5-dihydro-3H-[1,2,4]triazin-2-yl)-N-(1-hydroxy-cycloheptylmethyl)-benzamide | 478.8 |
| 54 | 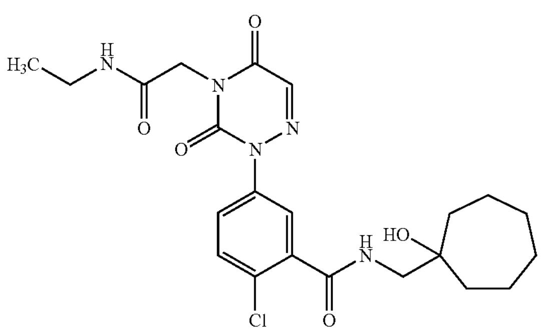 | 2-Chloro-5-(4-ethylcarbamoylmethyl-3,5-dioxo-4,5-dihydro-3H-[1,2,4]triazin-2-yl)-N-(1-hydroxy-cycloheptylmethyl)-benzamide | 478.8 |
| 55 | 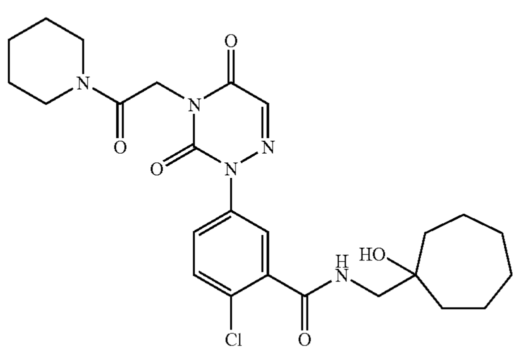 | 2-Chloro-5-[3,5-dioxo-4-(2-oxo-2-piperidin-1-yl-ethyl)-4,5-dihydro-3H-[1,2,4]triazin-2-yl]-N-(1-hydroxy-cycloheptylmethyl)-benzamide | 518.8 |

TABLE 2-continued

| EXAMPLE | STRUCTURE | NAME | DATA LCMS M/Z |
|---|---|---|---|
| 56 | 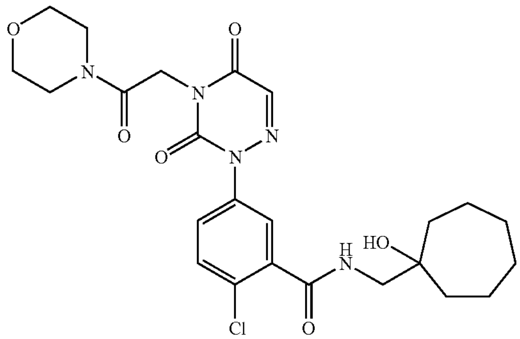 | 2-Chloro-N-(1-hydroxy-cycloheptylmethyl)-5-[4-(2-morpholin-4-yl-2-oxo-ethyl)-3,5-dioxo-4,5-dihydro-3H-[1,2,4]triazin-2-yl]-benzamide | 520.8 |
| 57 | 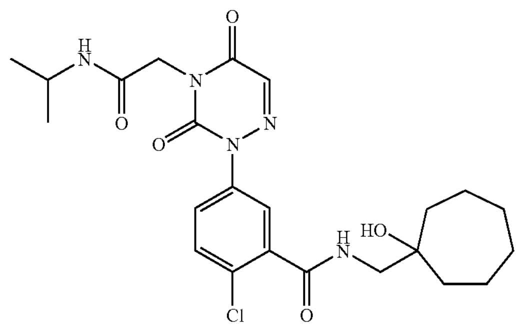 | 2-Chloro-N-(1-hydroxy-cycloheptylmethyl)-5-[4-(isopropylcarbamoyl-methyl)-3,5-dioxo-4,5-dihydro-3H-[1,2,4-triazin-2-yl]-benzamide | 492.8 |
| 58 | 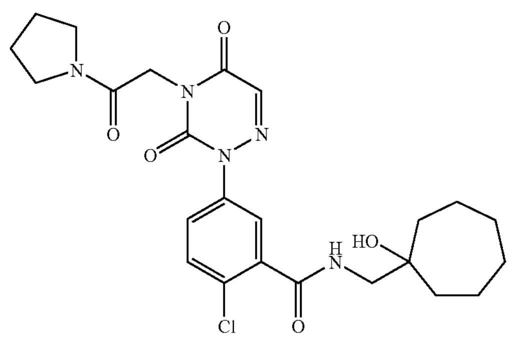 | 2-Chloro-5-[3,5-dioxo-4-(2-oxo-2-pyrrolidin-1-yl-ethyl)-4,5-dihydro-3H-[1 2,4]triazin-2-yl]-N-(1-hydroxy-cycloheptylmethyl)-benzamide | 504.4 |
| 59 | 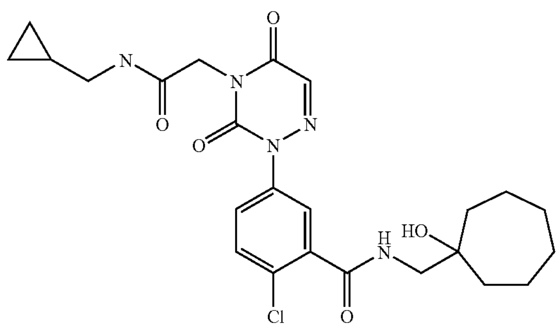 | 2-Chloro-5-{4-[(cyclopropylmethyl-carbamoyl)-methyl]-3,5-dioxo-4,5-dihydro-3H-[1,2,4]triazin-2-yl}-N-(1-hydroxy-cycloheptylmethyl)-benzamide | 504.4 |

TABLE 2-continued

| EXAMPLE | STRUCTURE | NAME | DATA LCMS M/Z |
|---|---|---|---|
| 60 | 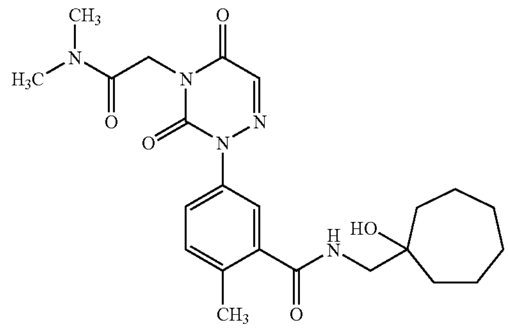 | 5-(4-Dimethylcarbamoylmethyl-3,5-dioxo-4,5-dihydro-3H-[1,2,4]triazin-2-yl)-N-(1-hydroxy-cycloheptylmethyl)-2-methyl-benzamide | 458.5 |

EXAMPLE 61

2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide

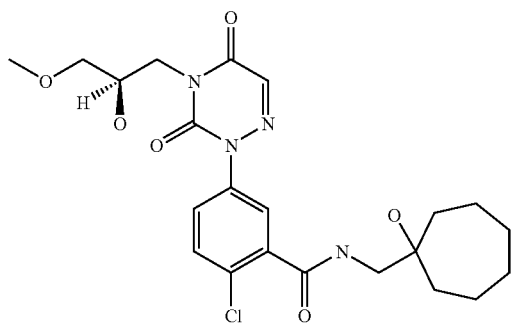

A) 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide 5-(3,5-Dioxo-4,5-dihydro-3H-[1,2,4]triazin-2-yl)-N-(1-hydroxy-cycloheptylmethyl)-2-methyl-benzamide (1.77 g, 4.5 mmol) and R-(−)-glycidyl methyl ether (2.5 mL, 27.8 mmol) in DMF (4.5 mL) were heated at 60° C. for 18 hours. The reaction was cooled, diluted with 1N HCl, and extracted with CH$_2$Cl$_2$. The organics were combined, washed with sat'd sodium bicarbonate, dried over sodium sulfate and charcoal, filtered, and concentrated in vacuo. The crude was purified by silica gel flash chromatography (elution with EtOAc), then recrystallized from ethyl acetate/hexane to give the title compound (1.62 g). LCMS (m/z) 479.5 M−1.

The compounds of Examples 62-99, identified in Table 3 below, can be prepared according to the method of Example 61.

TABLE 3

| EXAMPLE | STRUCTURE | NAME | DATA LCMS M/Z |
|---|---|---|---|
| 62 | 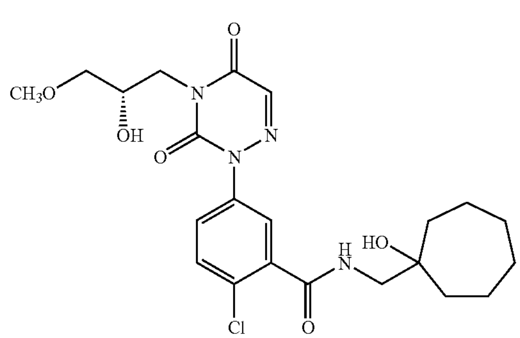 | 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide | 481.5 |

TABLE 3-continued

| EXAMPLE | STRUCTURE | NAME | DATA LCMS M/Z |
|---|---|---|---|
| 63 | 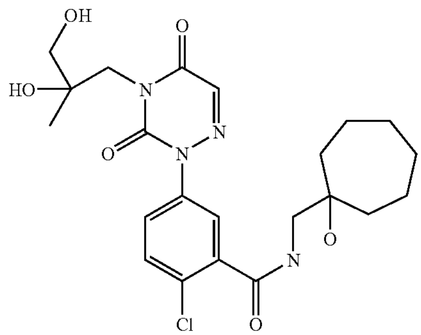 | 2-Chloro-5-[4-(2,3-dihydroxy-2-methyl-propyl)-3,5-dioxo-4,5-dihydro-3H-[1,2,4]triazin-2-yl]-N-(1-hydroxy-cycloheptylmethyl)-benzamide | 481.6 |
| 64 | 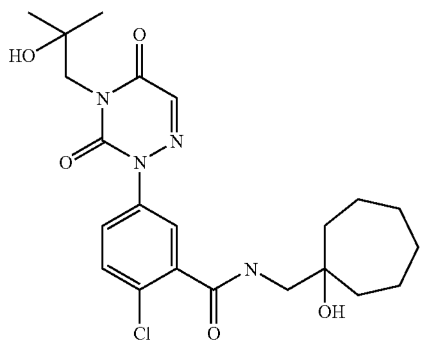 | 2-Chloro-N-(1-hydroxy-cycloheptylmethyl)-5-[4-(2-hydroxy-2-methyl-propyl)-3,5-dioxo-4,5-dihydro-3H-[1,2,4]triazin-2-yl]-benzamide | 465.5 |
| 65 | 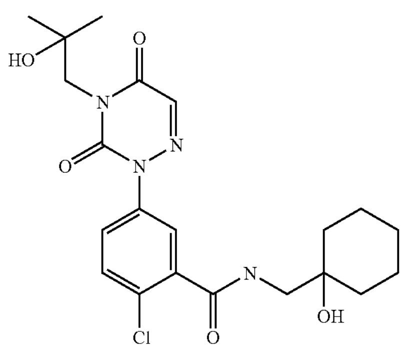 | 2-Chloro-N-(1-hydroxy-cyclohexylmethyl)-5-[4-(2-hydroxy-2-methyl-propyl)-3,5-dioxo-4,5-dihydro-3H-[1,2,4]triazin-2-yl]-benzamide | 451.5 |
| 66 | 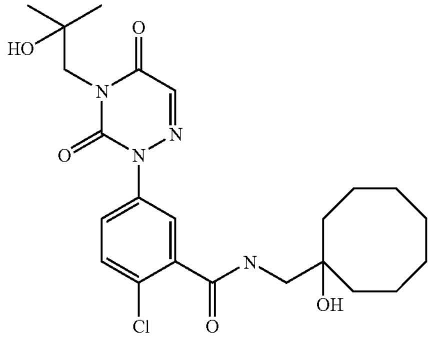 | 2-Chloro-N-(1-hydroxy-cyclooctylmethyl)-5-[4-(2-hydroxy-2-methyl-propyl)-3,5-dioxo-4,5-dihydro-3H-[1,2,4]triazin-2-yl]-benzamide | 479.4 |

TABLE 3-continued

| EXAMPLE | STRUCTURE | NAME | DATA LCMS M/Z |
|---|---|---|---|
| 67 | 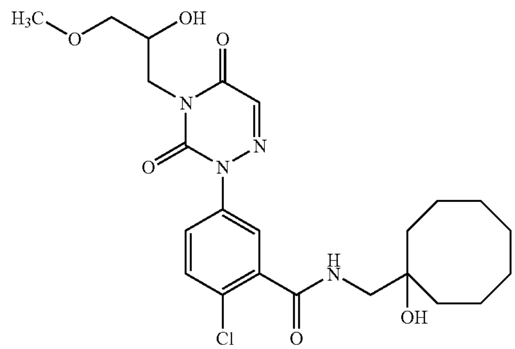 | 2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide | 495.6 |
| 68 | 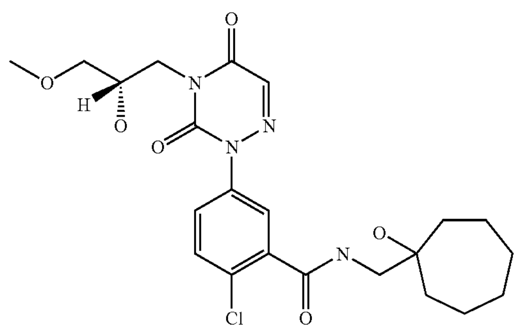 | 2-Chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide | 479.4 (M − 1) |
| 69 | 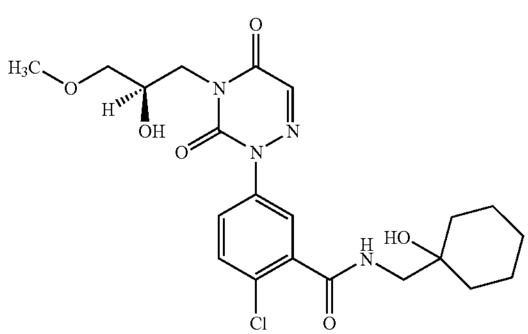 | 2-Chloro-N-(1-hydroxy-cyclohexylmethyl)-5-[4-(2-hydroxy-3-methoxy-propyl)-3,5-dioxo-4,5-dihydro-3H-[1,2,4]triazin-2-yl]-benzamide | 467.5 |
| 70 | 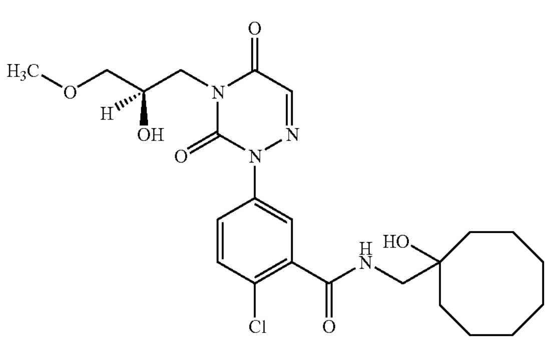 | 2-Chloro-N-(1-hydroxy-cyclooctylmethyl)-5-[4-(2-hydroxy-3-methoxy-propyl)-3,5-dioxo-4,5-dihydro-3H-[1,2,4]triazin-2-yl]-benzamide | 495.6 |

TABLE 3-continued

| EXAMPLE | STRUCTURE | NAME | DATA LCMS M/Z |
|---|---|---|---|
| 71 | 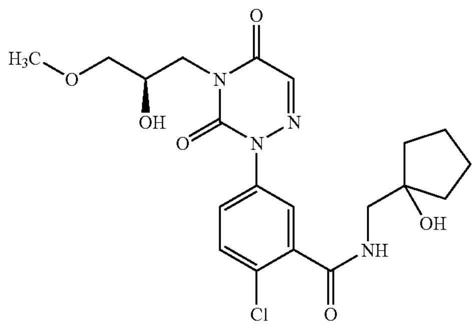 | 2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide | 453.5 |
| 72 | 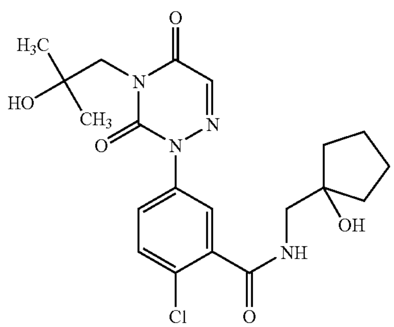 | 2-Chloro-N-(1-hydroxy-cyclopentylmethyl)-5-[4-(2-hydroxy-2-methyl-propyl)-3,5-dioxo-4,5-dihydro-3H-[1,2,4]triazin-2-yl]-benzamide | 437.4 |
| 73 | 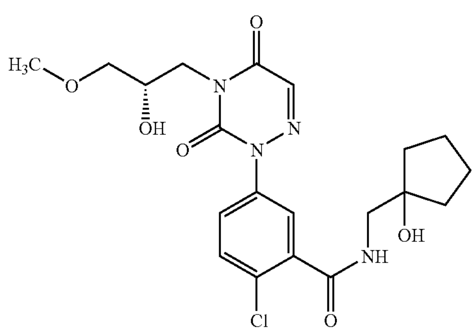 | 2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide | 453.5 |
| 74 | 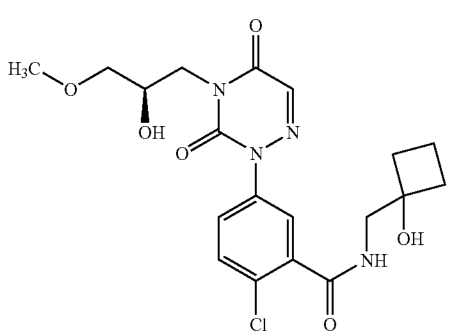 | 2-Chloro-N-(1-hydroxy-cyclobutylmethyl)-5-[4-(2-hydroxy-3-methoxy-propyl)-3,5-dioxo-4,5-dihydro-3H-[1,2,4]triazin-2-yl]-benzamide | 439.5 |

TABLE 3-continued

| EXAMPLE | STRUCTURE | NAME | DATA LCMS M/Z |
|---|---|---|---|
| 75 | 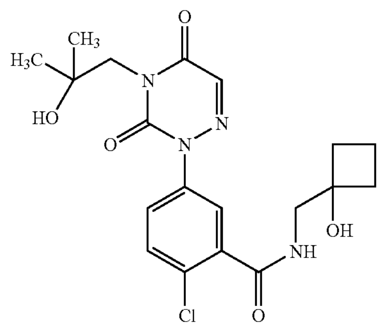 | 2-Chloro-N-(1-hydroxy-cyclobutylmethyl)-5-[4-(2-hydroxy-2-methyl-propyl)-3,5-dioxo-4,5-dihydro-3H-[1,2,4]triazin-2-yl]-benzamide | 423.3 |
| 76 | 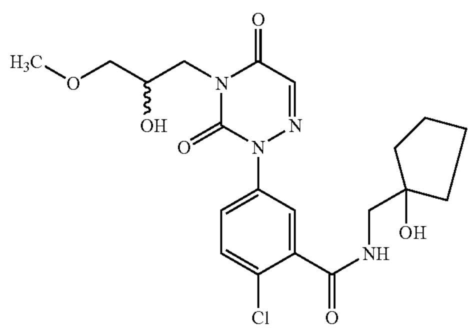 | 2-Chloro-N-(1-hydroxy-cyclopentylmethyl)-5-[4-(2-hydroxy-3-methoxy-propyl)-3,5-dioxo-4,5-dihydro-3H-[1,2,4]triazin-2-yl]-benzamide | 453.5 |
| 77 | 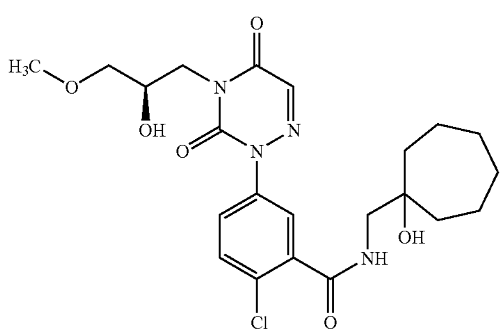 | 2-Chloro-5-[4-(2-hydroxy-3-methoxy-propyl)-3,5-dioxo-4,5-dihydro-3H-[1,2,4]triazin-2-yl]-N-(1-hydroxymethyl-cycloheptylmethyl)-benzamide | 495.4 |
| 78 | 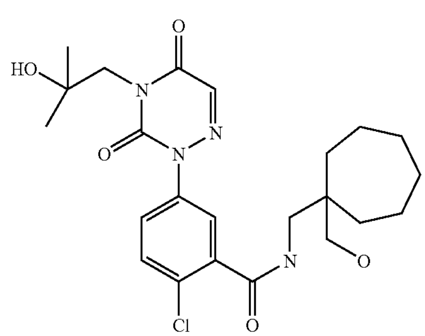 | 2-Chloro-N-(1-hydroxymethyl-cycloheptylmethyl)-5-[4-(2-hydroxy-2-methyl-propyl)-3,5-dioxo-4,5-dihydro-3H-[1,2,4]triazin-2-yl]-benzamide | 479.4 |

TABLE 3-continued

| EXAMPLE | STRUCTURE | NAME | DATA LCMS M/Z |
|---|---|---|---|
| 79 | 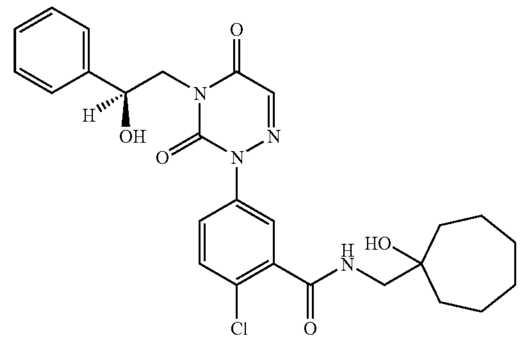 | 2-Chloro-N-(1-hydroxy-cycloheptylmethyl)-5-[4-(2-hydroxy-2-phenyl-propyl)-3,5-dioxo-4,5-dihydro-3H-[1,2,4]triazin-2-yl]-benzamide | 513.4 |
| 80 | 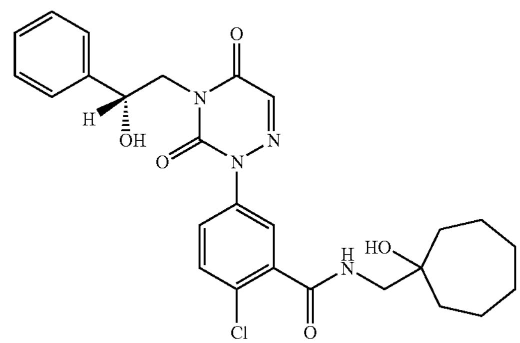 | 2-Chloro-N-(1-hydroxy-cycloheptylmethyl)-5-[4-(2-hydroxy-2-phenyl-ethyl)-3,5-dioxo-4,5-dihydro-3H-[1,2,4]triazin-2-yl]-benzamide | 513.3 |
| 81 | 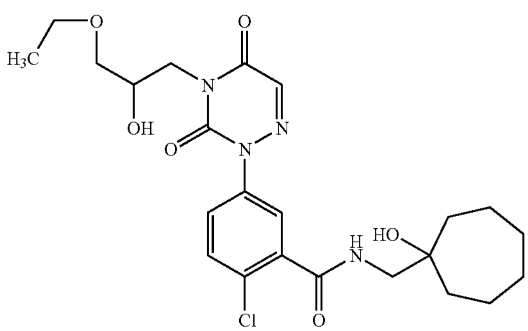 | 2-Chloro-5-[4-(3-ethoxy-2-hydroxy-propyl)-3,5-dioxo-4,5-dihydro-3H-[1,2,4]triazin-2-yl]-N-(1-hydroxy-cycloheptylmethyl)-benzamide | 495.4 |
| 82 | 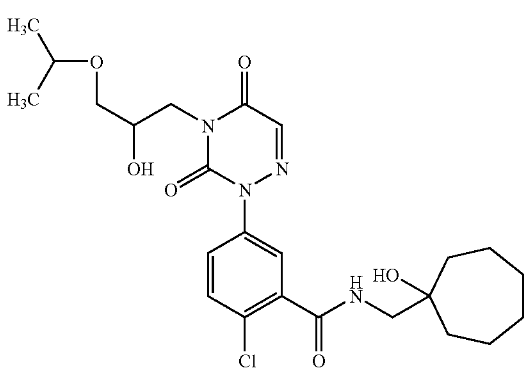 | 2-Chloro-N-(1-hydroxy-cycloheptylmethyl)-5-[4-(2-hydroxy-3-isopropoxy-propyl)-3,5-dioxo-4,5-dihydro-3H-[1,2,4]triazin-2-yl]-benzamide | 509.4 |

TABLE 3-continued

| EXAMPLE | STRUCTURE | NAME | DATA LCMS M/Z |
|---|---|---|---|
| 83 | 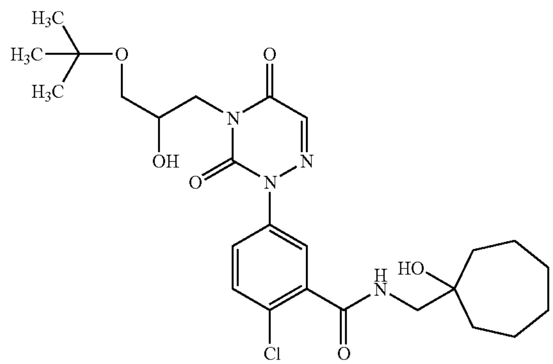 | 5-[4-(3-tert-Butoxy-2-hydroxy-propyl)-3,5-dioxo-4,5-dihydro-3H-[1,2,4]triazin-2-yl]-2-chloro-N-(1-hydroxy-cycloheptylmethyl)-benzamide | 523.4 |
| 84 | 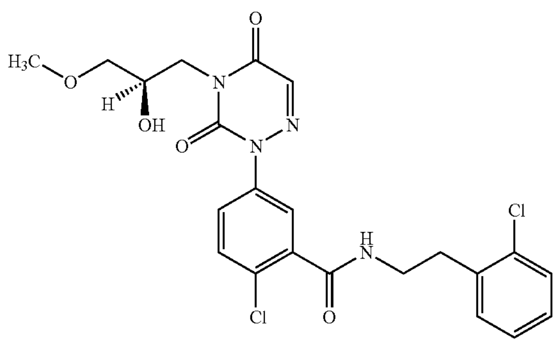 | 2-Chloro-N-[2-(2-chloro-phenyl)-ethyl]-5-[4-(2-hydroxy-3-methoxy-propyl)-3,5-dioxo-4,5-dihydro-3H-[1,2,4]triazin-2-yl]-benzamide | 494.4 |
| 85 | 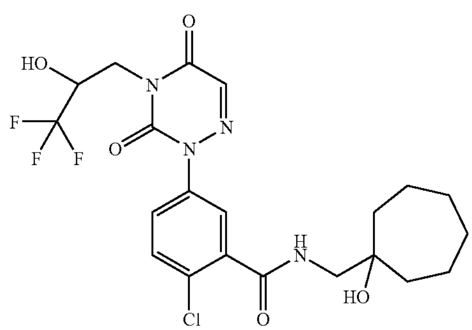 | 2-Chloro-5-[3,5-dioxo-4-(3,3,3-trifluoro-2-hydroxy-propyl)-4,5-dihydro-3H-[1,2,4]triazin-2-yl]-N-(1-hydroxy-cycloheptylmethyl)-benzamide | 505.3 |
| 86 | 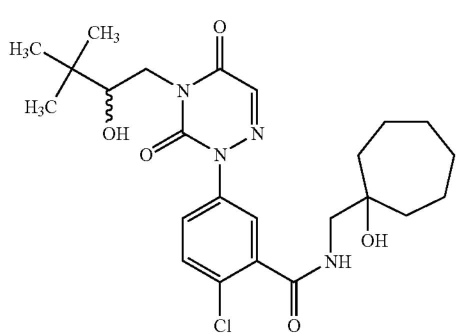 | 2-Chloro-N-(1-hydroxy-cycloheptylmethyl)-5-[4-(2-hydroxy-3,3-dimethyl-butyl)-3,5-dioxo-4,5-dihydro-3H-[1,2,4]triazin-2-yl]-benzamide | 493.4 |

TABLE 3-continued

| EXAMPLE | STRUCTURE | NAME | DATA LCMS M/Z |
|---|---|---|---|
| 87 | 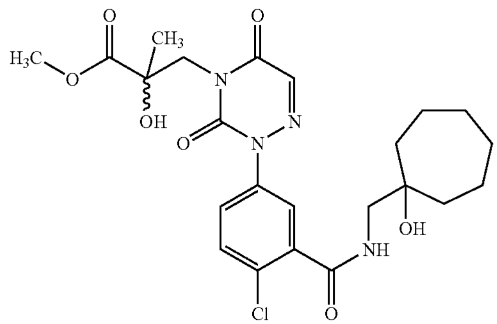 | 3-(2-{4-Chloro-3-[(1-hydroxy-cycloheptylmethyl)-carbamoyl]-phenyl}-3,5-dioxo-2-5-dihydro-3H-[1,2,4]triazin-4-yl)-2-hydroxy-2-methyl-propionic acid methyl ester | 509.4 |
| 88 | 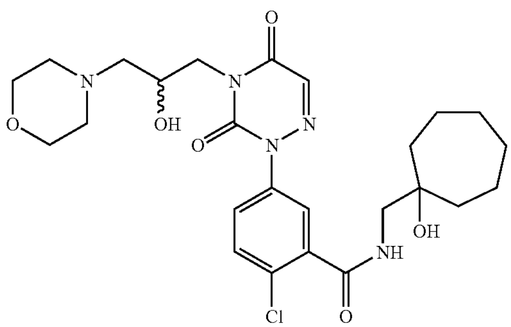 | 2-Chloro-N-(1-hydroxy-cycloheptylmethyl)-5-[4-(2-hydroxy-3-morpholin-4-yl-propyl)-3,5-dioxo-4,5-dihydro-3H-[1,2,4]triazin-2-yl]-benzamide | 536.4 |
| 89 | 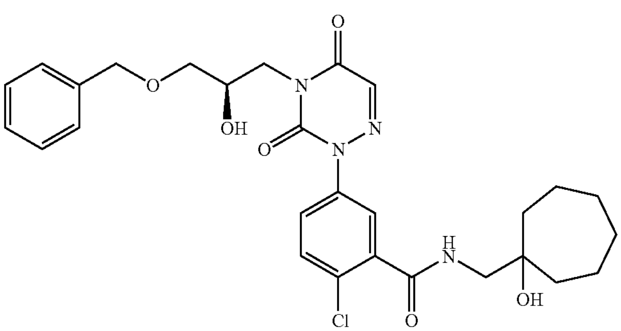 | 5-[4-(3-Benzyloxy-2-hydroxy-propyl)-3,5-dioxo-4,5-dihydro-3H-[1,2,4]triazin-2-yl]-2-chloro-N-(1-hydroxy-cycloheptylmethyl)-benzamide | 557.4 |
| 90 | 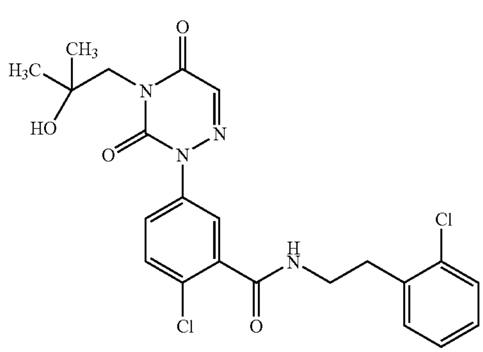 | 2-Chloro-N-[2-(2-chloro-phenyl)-ethyl]-5-[4-(2-hydroxy-2-methyl-propyl)-3,5-dioxo-4,5-dihydro-3H-[1,2,4]triazin-2-yl]-benzamide | 478.3 |

TABLE 3-continued

| EXAMPLE | STRUCTURE | NAME | DATA LCMS M/Z |
|---|---|---|---|
| 91 | 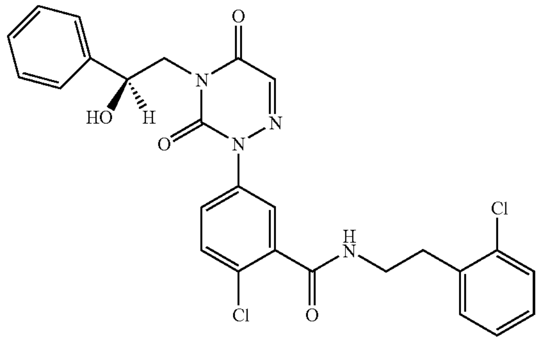 | 2-Chloro-N-[2-(2-chloro-phenyl)-ethyl]-5-[4-(2-hydroxy-2-phenyl-ethyl)-3,5-dioxo-4,5-dihydro-3H-[1,2,4]triazin-2-yl]-benzamide | 525.4 |
| 92 | 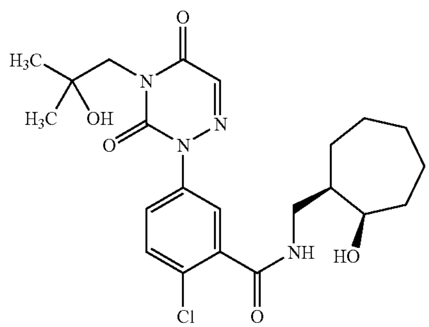 | 2-Chloro-N-(2-hydroxy-cycloheptylmethyl)-5-[4-(2-hydroxy-2-methyl-propyl)-3,5-dioxo-4,5-dihydro-3H-[1,2,4]triazin-2-yl]-benzamide | 465.4 |
| 93 | 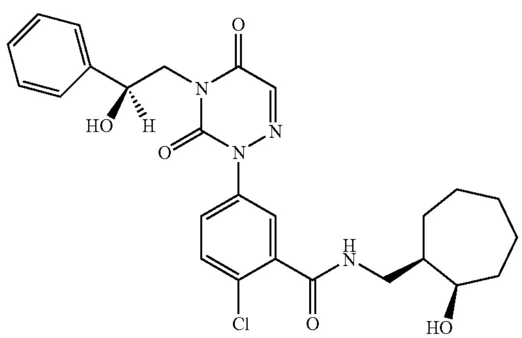 | 2-Chloro-N-(2-hydroxy-cycloheptylmethyl)-5-[4-(2-hydroxy-2-phenyl-ethyl)-3,5-dioxo-4,5-dihydro-3H-[1,2,4]triazin-2-yl]-benzamide | 513.4 |
| 94 | 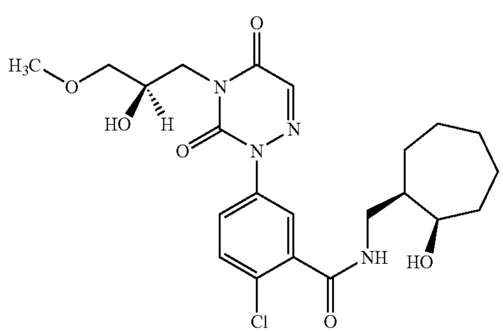 | 2-Chloro-N-(2-hydroxy-cycloheptylmethyl)-5-[4-(2-hydroxy-3-methoxy-propyl)-3,5-dioxo-4,5-dihydro-3H-[1,2,4]triazin-2-yl]-benzamide | 481.4 |

TABLE 3-continued

| EXAMPLE | STRUCTURE | NAME | DATA LCMS M/Z |
|---|---|---|---|
| 95 | 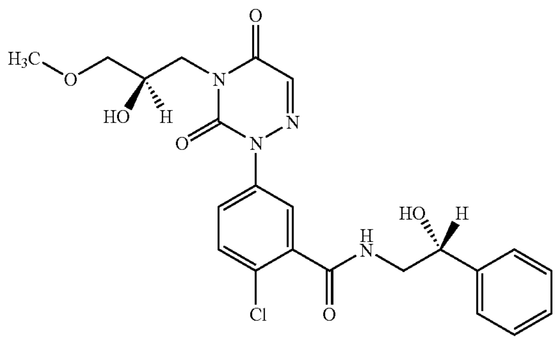 | 2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide | 475.3 |
| 96 | 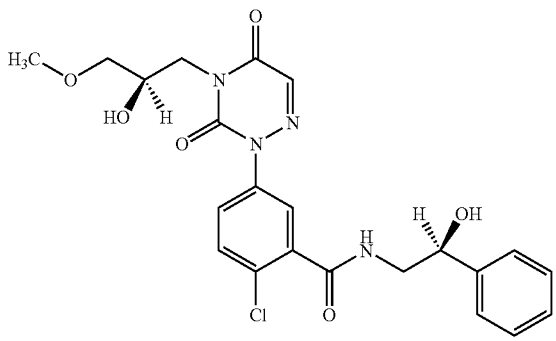 | 2-Chloro-5-[4-(2-hydroxy-3-methoxy-propyl)-3,5-dioxo-4,5-dihydro-3H-[1,2,4]triazin-2-yl]-N-(2-hydroxy-2-phenyl-ethyl)-benzamide | 475.3 |
| 97 | 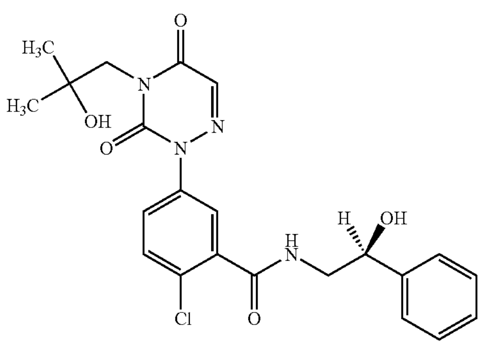 | 2-Chloro-5-[4-(2-hydroxy-2-methyl-propyl)-3,5-dioxo-4,5-dihydro-3H-[1,2,4]triazin-2-yl]-N-(2-hydroxy-2-phenyl-ethyl)-benzamide | 459.3 |
| 98 | 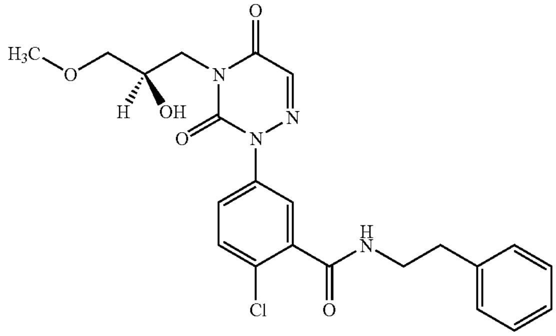 | 2-Chloro-5-[4-(2-hydroxy-3-methoxy-propyl)-3,5-dioxo-4,5-dihydro-3H-[1,2,4]triazin-2-yl]-N-phenethyl-benzamide | 459.2 |

TABLE 3-continued

| EXAMPLE | STRUCTURE | NAME | DATA LCMS M/Z |
|---|---|---|---|
| 99 | 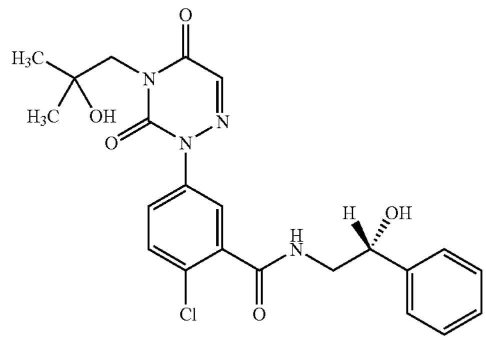 | 2-Chloro-5-[4-(2-hydroxy-2-methyl-propyl)-3,5-dioxo-4,5-dihydro-3H-[1,2,4]triazin-2-yl]-N-hydroxy-2-phenyl-ethyl)-benzamide | 459.3 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

The invention claimed is:

1. A method of treating asthma in a mammal in need thereof, comprising administering to said mammal a therapeutically effective amount of 2-chloro-N-(1-hydroxy-cycloheptylmethyl)-5-[4-(2-hydroxy-3-methoxy-propyl)-3,5-dioxo-4,5-dihydro-3H-[1,2,4]triazin-2-yl]-benzamide, or a pharmaceutically acceptable salt thereof.

2. A method of treating asthma in a mammal in need thereof, comprising administering to said mammal a therapeutically effective amount of 2-chloro-N-(1-hydroxy-cycloheptylmethyl)-5-[4-(2-(R)-hydroxy-3-methoxy-propyl)-3,5-dioxo-4,5-dihydro-3H-[1,2,4]triazin-2-yl]-benzamide, or a pharmaceutically acceptable salt thereof.

3. A method of treating asthma in a mammal in need thereof, comprising administering to said mammal a therapeutically effective amount of 2-chloro-N-(1-hydroxy-cycloheptylmethyl)-5-[4-(2-(S)-hydroxy-3-methoxy-propyl)-3,5-dioxo-4,5dihydro-3H-[1,2,4]triazin-2-yl]-benzamide, or a pharmaceutically acceptable salt thereof.

* * * * *